United States Patent [19]
Bird et al.

[11] Patent Number: 5,478,842
[45] Date of Patent: Dec. 26, 1995

[54] ETHER DERIVATIVES HAVING 5-LIPOXYGENASE INHIBITORY ACTIVITY

[75] Inventors: Thomas G. C. Bird, Witry-Les-Reims, France; Graham C. Crawley, Cheshire, United Kingdom; Michael S. Large, Staffordshire, United Kingdom; Patrick Ple, Reims, France

[73] Assignees: Zeneca Limited, London, England; Zeneca Pharma S.A., Cergy Cedex, France

[21] Appl. No.: 234,148

[22] Filed: Apr. 28, 1994

[30] Foreign Application Priority Data

| Apr. 29, 1993 | [EP] | European Pat. Off. | 93401120 |
| Aug. 2, 1993 | [EP] | European Pat. Off. | 93401991 |
| Jan. 28, 1994 | [EP] | European Pat. Off. | 94400190 |

[51] Int. Cl.$^6$ .......... A61K 31/47; A61K 31/40; C07D 405/14; C07D 405/12
[52] U.S. Cl. .......... 514/312; 514/221; 514/311; 514/369; 514/414; 540/523; 546/157; 546/158; 548/181; 548/467
[58] Field of Search .......... 514/311, 312, 514/369, 414; 548/181, 467; 546/157, 158

[56] References Cited

U.S. PATENT DOCUMENTS

| 4,567,184 | 1/1986 | Musser et al. | 514/277 |
| 4,625,034 | 11/1986 | Neiss et al. | 514/152 |
| 4,631,287 | 12/1986 | Chakraborty et al. | 514/307 |
| 4,725,619 | 2/1988 | Chakraborty et al. | 514/44.2 |
| 4,728,668 | 3/1988 | Chakraborty et al. | 514/314 |
| 4,794,188 | 12/1988 | Musser et al. | 514/152 |
| 4,839,369 | 6/1989 | Yowssefyeh et al. | 514/314 |
| 4,868,193 | 9/1989 | Lee | 514/314 |
| 4,874,769 | 10/1989 | Youssefyeh et al. | 514/314 |
| 5,098,930 | 3/1992 | Edwards et al. | 514/459 |
| 5,134,148 | 7/1992 | Crawley et al. | 514/312 |
| 5,202,326 | 4/1993 | Crawley et al. | 514/255 |
| 5,208,259 | 5/1993 | Bird et al. | 514/312 |
| 5,217,969 | 6/1993 | Bruneau et al. | 514/230.5 |
| 5,217,978 | 6/1993 | Bird | 514/312 |
| 5,221,677 | 6/1993 | Crawley et al. | 514/309 |
| 5,225,438 | 7/1993 | Dowell et al. | 514/459 |
| 5,234,950 | 8/1993 | Edwards et al. | 514/473 |
| 5,236,919 | 8/1993 | Crawley et al. | 514/349 |
| 5,240,941 | 8/1993 | Bruneau | 514/312 |
| 5,272,173 | 12/1993 | Dowell et al. | 514/459 |
| 5,276,037 | 1/1994 | Dowell et al. | 514/253 |
| 5,302,594 | 4/1994 | Crawley et al. | 514/249 |
| 5,308,852 | 5/1994 | Girard et al. | 514/336 |
| 5,321,025 | 6/1994 | Bruneau et al. | 514/224.2 |

FOREIGN PATENT DOCUMENTS

| 0501578 | 9/1992 | European Pat. Off. | C07D 309/10 |
| 0501579 | 9/1992 | European Pat. Off. | C07D 407/12 |

*Primary Examiner*—Jacqueline Haley
*Attorney, Agent, or Firm*—Cushman Darby & Cushman

[57] ABSTRACT

The invention concerns ether derivatives of the formula I $$Q^1-X-Ar-Q^2 \quad \text{I}$$

wherein $Q^1$ is an optionally substituted 9-, 10- or 11-membered bicyclic heterocyclic moiety containing one or two nitrogen heteroatoms and optionally containing a further heteroatom selected from nitrogen, oxygen and sulphur;

X is oxy, thio, sulphinyl or sulphonyl;

Ar is optionally substituted phenylene, pyridinediyl, pyrimidinediyl, thiophenediyl, furandiyl, thiazolediyl, oxazoiediyl, thiadiazoiediyl or oxadiazolediyl; and $Q^2$ is selected from the groups of the formulae II and III:

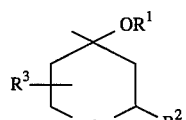

II

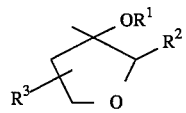

III wherein $R^1$ is hydrogen, (2–5C)alkanoyl or optionally substituted benzoyl;

$R^2$ is (1–4C)alkyl; and $R^3$ is hydrogen or (1–4C)alkyl;

or $R^2$ and $R^3$ are linked to form a methylene, vinylene, ethylene or trimethylene group;

or a pharmaceutically-acceptable salt thereof;

processes for their preparation; pharmaceutical compositions containing them and their use as 5-lipoxygenase inhibitors.

11 Claims, No Drawings

ETHER DERIVATIVES HAVING 5-LIPOXYGENASE INHIBITORY ACTIVITY

This invention concerns ether derivatives and more particularly ether derivatives which are inhibitors of the enzyme 5-lipoxygenase (hereinafter referred to as 5-L0). The invention also concerns processes for the manufacture of said ether derivatives and novel pharmaceutical compositions containing them. Also included in the invention is the use of said ether derivatives in the treatment of various diseases such as inflammatory and/or allergic diseases in which the direct or indirect products of 5-L0 catalysed oxidation of arachidonic acid are involved, and the production of new medicaments for such use.

As stated above the ether derivatives described hereinafter are inhibitors of 5-L0, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various diseases, for example various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin diseases (especially psoriasis, eczema and dermatitis), ocular conditions (especially allergic conjunctivitis and uveitis) and respiratory disease (especially asthma, bronchitis and allergic rhiniris), for example in the production and development of various cardiovascular and cerebrovascular disorders such as myocardial infarction, the formation of atherosclerotic plaques, hypertension, platelet aggregation, angina, stroke, repertusion injury, vascular injury including restenosis and peripheral vascular disease, for example in the formation of the conditions of shock or trauma such as can follow burn injuries, toxaemia or surgery, and for example various disorders of bone metabolism such as osteoporosis (including senile and postmenopausal osteoporosis), Paget's disease, bone metastases, hypercalcaemia, hyperparathyroidism, osteosclerosis, osteopetrosis and periodontitis, and the abnormal changes in bone metabolism which may accompany rheumatoid arthritis and osteoarthritis. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application No. 0385662 that certain heterocyclic derivatives possess inhibitory properties against 5-LO. Furthermore European Patent Applications Nos. 0420511, 0462812 and 0462813 are also concerned with heterocyclic derivatives which possess inhibitory properties against 5-L0. We have now discovered that certain ether derivatives, which possess some structural features which are similar to those of the compounds disclosed in the above-mentioned applications but which possess other structural features in particular an alcohol group which was not identified in those earlier applications, are effective inhibitors of the enzyme 5-LO and thus of leukotriene biosyntheses. Thus such compounds are of value as therapeutic agents in the treatment of, for example, allergic conditions, psoriasis, asthma, cardiovascular and cerebrovascular disorders, and/or inflammatory and arthritic conditions, and/or disorders of bone metabolism, mediated alone or in part by one or more leukotrienes.

It has also been found that certain compounds disclosed in European Patent Application No. 0462812 possess the undesirable property of auto-induction i.e. the repeated dosing of such a compound to a warm-blooded animal results in an increase in the efficiency with which the animal's hepatic enzymes metabolise the compound. The result is a decrease on repeat dosing of the quantity of the compound present in the animal's blood stream as shown, for example, by a decrease in the maximum concentration achieved (C max) or, for example, a decrease in the exposure of the animal to the compound as measured by the area under the curve (AUC) of a plot of the concentration of the compound in the blood stream versus time after dosing. The compound 4-methoxy-4-[5-(1-methyl-2-oxo-1,2,3,4-tetrahydroquinolin-6-ylthio)thien-2-yl]tetrahydropyran possesses the undesirable property of auto-induction.

It has also been found that certain compounds disclosed in European Patent Application No. 0462812 are non-crystalline, for example they are formed in an oily or gummy state or they are isolated as foams. Such non-crystalline compounds are undesirable when consideration is given toward the preparation, purification, analysis, handling and formulation of larger quantities of the compounds. The compound (2S,4R)-4-methoxy-2-methyl-4-[5-(1-methyl-2-thioxo-1,2,3,4-tetrahydroquinolin-6-ylthio)thien-2-yl]tetrahydropyran possesses the undesirable property of being a viscous oil.

According to one aspect of the invention there is provided an ether derivative of the formula I $$Q^1—X—Ar—Q^2 \qquad\qquad I$$

wherein $Q^1$ is a 9-, 10- or 11-membered bicyclic heterocyclic moiety containing one or two nitrogen heteroatoms and optionally containing a further heteroatom selected from nitrogen, oxygen and sulphur, and $Q^1$ may optionally bear up to four substituents selected from halogeno, hydroxy, cyano, formyl, oxo, thioxo, (1–4C)alkyl, (3–4C)alkenyl, (3–4C)alkynyl, (1–4C)alkoxy, fluoro-(1–4C)alkyl, hydroxy-(1–4C)alkyl, (2–5C)alkanoyl, phenyl, benzoyl and benzyl, and wherein said phenyl, benzoyl and benzyl substituents may optionally bear one or two substituents selected from halogeno, (1–4C)alkyl and (1–4C)alkoxy;

X is oxy, thio, sulphinyl or sulphonyl;

Ar is phenylene, pyridinediyl, pyrimidinediyl, thiophenediyl, furandiyl, thiazolediyl, oxazolediyl, thiadiazolediyl or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino; and $Q^2$ is selected from the groups of the formulae II and III:

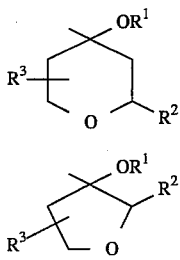

wherein $R^1$ is hydrogen, (2–5C)alkanoyl or benzoyl, and wherein said benzoyl group may optionally bear one or two substituents selected from halogeno, (1–4C)alkyl and (1–4C)alkoxy;

$R^2$ is (1–4C)alkyl; and $R^3$ is hydrogen or (1–4C)alkyl;

or $R^2$ and $R^3$ are linked to form a methylene, vinylene, ethylene or trimethylene group;

or a pharmaceutically-acceptable salt thereof.

According to a further aspect of the invention there is provided an ether derivative of the formula I $$Q^1\text{—}X\text{—}Ar\text{—}Q^2 \qquad I$$

wherein $Q^1$ is a 10-membered bicyclic heterocyclic moiety containing one or two nitrogen heteroatoms and optionally containing a further heteroatom selected from nitrogen, oxygen and sulphur, and $Q^1$ may optionally bear up to four substituents selected from halogeno, hydroxy, cyano, formyl, oxo, thioxo, (1–4C)alkyl, (1–4C)alkoxy, fluoro-(1–4C)alkyl, hydroxy-(1–4C)alkyl, (2–5C)alkanoyl, phenyl, benzoyl and benzyl, and wherein said phenyl, benzoyl and benzyl substituents may optionally bear one or two substituents selected from halogeno, (1–4C)alkyl and (1–4C)alkoxy;

X is oxy, thio, sulphinyl or sulphonyl;

Ar is phenylene, pyridinediyl, pyrimidinediyl, thiophenediyl, furandiyl, thiazolediyl, oxazolediyl, thiadiazolediyl or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino; and $Q^2$ is selected from the groups of the formulae II and III:

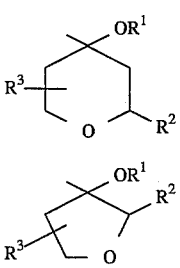

wherein $R^1$ is hydrogen, (2–5C)alkanoyl or benzoyl, and wherein said benzoyl group may optionally bear one or two substituents selected from halogeno, (1–4C)alkyl and (1–4C)alkoxy;

$R^2$ is (1–4C)alkyl; and $R^3$ is hydrogen or (1–4C)alkyl;

or a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-L0 and is not to be limited merely to any one tautomeric form utilised within the formulae drawings.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-L0. The synthesis of optically active forms may be carried out by standard techniques of organic chemistry well known in the art, for example by synthesis from optically active starting materials or by resolution of a racemic form.

Suitable values for the generic terms referred to above include those set out below.

A suitable value for $Q^1$ when it is a 9-membered bicyclic heterocyclic moiety containing one or two nitrogen heteroatoms and optionally containing a further heteroatom selected from nitrogen, oxygen and sulphur is, for example, a benzo-fused heterocyclic moiety or a hydrogenated derivative thereof such as indolyl, indolinyl, isoindolyl, isoindolinyl, indolizinyl, benzimidazolyl, 2,3-dihydrobenzimidazolyl, 1H-indazolyl, 2,3-dihydro-1H-indazolyl, benzoxazolyl, 2,3-dihydrobenzoxazolyl, benzo[c]isoxazolyl, benzo[d]isoxazolyl, 2,3-dihydrobenzo[d]isoxazolyl, benzothiazolyl, 2,3-dihydrobenzothiazolyl, benzo[c]isothiazolyl, benzo[d]isothiazolyl and 2,3-dihydrobenzo[d]isothiazolyl, or, for example, a pyrido-fused heterocyclic moiety or a hydrogenated derivative thereof such as 1H-pyrrolo[2,3-b]pyridyl, 2,3-dihydro-1H-pyrrolo[2,3-b]pyridyl, 1H-pyrrolo[2,3-c]pyridyl, 2,3-dihydro-1H-pyrrolo[2,3-c]pyridyl, 1H-imidazo[4,5-b]pyridyl, 2,3-dihydro-1H-imidazo[4,5-b]pyridyl, 1H-imidazo[4,5-c]pyridyl and 2,3-dihydro-1H-imidazo[4,5-c]pyridyl.

A suitable value for $Q^1$ when it is a 10-membered bicyclic heterocyclic moiety containing one or two nitrogen heteroatoms and optionally containing a further heteroatom selected from nitrogen, oxygen and sulphur is, for example, a 10-membered benzo-fused heterocyclic moiety such as quinolyl, isoquinolyl, cinnolinyl, quinazolinyl, quinoxalinyl, 4H-1,4-benzoxazinyl or 4H-1,4-benzothiazinyl, or a hydrogenated derivative thereof such as 1,2-dihydroquinolyl, 1,2,3,4-tetrahydroquinolyl, 1,2-dihydroisoquinolyl, 1,2,3,4-tetrahydroquinazolinyl, 2 3-dihydro-4H-1,4-benzoxazinyl or 2,3-dihydro-4H-1,4-benzothiazinyl; or, for example, a 10-membered pyrido-fused heterocyclic moiety such as 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof. A suitable value for $Q^1$ when it is an 11-membered bicyclic heterocyclic moiety containing one or two nitrogen heteroatoms and optionally containing a further heteroatom selected from nitrogen, oxygen and sulphur is, for example, an 11-membered benzo-fused heterocyclic moiety such as 1H-benzo[b]azepine, or a hydrogenated derivative thereof such as 2,3,4,5-tetrahydro-1H-benzo[b]azepine.

The heterocyclic moiety may be attached through any available position including from either of the two rings of the bicyclic heterocyclic moiety and including through an available nitrogen atom. The heterocyclic moiety may bear a suitable substituent such as, for example, a (1–4C)alkyl, (3–4C)alkenyl, (3–4C)alkynyl, fluoro-(1–4C)alkyl, phenyl, benzoyl or benzyl substituent on an available nitrogen atom.

Suitable values for substituents which may be present on $Q^1$ or Ar, on the phenyl substituent on $Q^1$, on any of the substituents on $Q^1$ which contain a phenyl group, or on $R^1$ when is benzoyl include, for example:

for halogeno: fluoro, chloro, bromo and iodo;

for (1–4C)alkyl: methyl, ethyl, propyl, isopropyl, butyl, isobutyl, sec-butyl and tert-butyl;

for (3–4C)alkenyl: allyl, 2-butenyl and 3-butenyl;

for (3–4C)alkynyl: 2-propynyl and 2-butynyl;

for (1–4C)alkoxy: methoxy, ethoxy, propoxy, isopropoxy and butoxy;

for fluoro-(1–4C)alkyl: fluoromethyl, difluoromethyl, trifluoromethyl, 2-fluoroethyl, 2,2,2-trifluoroethyl and pentafluoroethyl;

for hydroxy-(1–4C)alkyl: hydroxymethyl, 2-hydroxyethyl and 3-hydroxypropyl;

for (2–5C)alkanoyl: acetyl, propionyl and butyryl;

for (1–4C)alkylamino: methylamino, ethylamino and propylamino; and for di-(1–4C)alkylamino: dimethylamino, diethylamino and N-ethyl-N-methylamino.

A suitable value for Ar when it is phenylene is, for example, 1,3- or 1,4-phenylene.

A suitable value for Ar when it is pyridinediyl, pyrimidinediyl, thiophenediyl, furandiyl, thiazolediyl, oxazolediyl, thiadiazolediyl or oxadiazolediyl is, for example, 2,4-, 2,5- or 3,5-pyridinediyl, 4,6-pyrimidinediyl, 2,4- or 2,5-thiophenediyl, 2,4- or 2,5-furandiyl, 2,4- or 2,5-thiazolediyl, 2,4- or 2,5-oxazolediyl, 2,5-thiadiazolediyl or 2,5-oxadiazolediyl.

A suitable value for $R^1$ when it is (2–5C)alkanoyl is, for example, acetyl, propionyl or butyryl.

A suitable value for $R^2$ or $R^3$ when it is (1–4C)alkyl is, for example, methyl, ethyl, propyl or isopropyl.

The substituent $R^3$ may be attached to any available carbon atom of the rings which form the group $Q^2$, including attachment to the carbon atom which carries the substituent $R^2$. When $R^2$ and $R^3$ are linked to form a methylene, vinylene, ethylene or trimethylene group, with the substituent $R^2$ located on one of the carbon atoms alpha to the oxygen atom of the rings which form the group $Q^2$, the substituent $R^3$ is preferably located on the other alpha carbon atom.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, ether derivatives of the formula I, or pharmaceutically-acceptable salts thereof, wherein:

(a) $Q^1$ is a 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to two further substituents selected from any of those substituents on $Q^1$ defined hereinbefore other than oxo or thioxo; and X, Ar and $Q^2$ have any of the meanings defined hereinbefore or in this section concerning particular compounds of the invention;

(b) $Q^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to three further substituents selected from fluoro, chloro, methyl, ethyl, allyl, 2-propynyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(c) $Q^1$ is 2-oxo-1,2-dihydroquinolinyl, 2-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H-1,4-benzoxazinyl which may optionally bear up to three substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(d) $Q^1$ is 2-oxo-1,2-dihydroquinolin-6-yl, 2-oxo-1,2,3,4-tetrahydroquinolin-6-yl or 3-oxo-2,3-dihydro-4H-1,4-benzoxazin-7-yl which may optionally bear up to three substituents selected from fluoro, chloro, methyl, ethyl, methoxy, ethoxy and trifluoromethyl; and X, Ar and $Q^2$ have any of the meanings defined hereinbefore or in this section concerning particular compounds of the invention;

(e) $Q^1$ is 2-oxo-1,2-dihydroquinolin-6-yl or 2-oxo-1,2,3,4-tetrahydroquinolin-6-yl which bears at the 1-position a substituent selected from methyl, ethyl, propyl, allyl and 2-propynyl; and X, Ar and $Q^2$ have any of the meanings defined hereinbefore or in this section concerning particular compounds of the invention;

(f) $Q^1$ is a 9-membered benzo-fused heterocyclic moiety containing one or two nitrogen heteroatoms and optionally containing a further heteroatom selected from oxygen and sulphur, which heterocyclic moiety may optionally bear one oxo or thioxo substituent and up to three further substituents selected from any of those substituents on $Q^1$ defined hereinbefore other than oxo or thioxo; and X, Ar and $Q^2$ have any of the meanings defined hereinbefore or in this section concerning particular compounds of the invention;

(g) $Q^1$ is indolyl, indolinyl, benzimidazolyl, 2,3-dihydrobenzimidazolyl, benzoxazolyl, 2,3-dihydrobenzoxazolyl, benzothiazolyl or 2,3-dihydrobenzothiazolyl which may optionally bear one oxo or thioxo substituent and up to three further substituents selected from fluoro, chloro, methyl, ethyl, allyl, 2-propynyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(h) $Q^1$ is 2-oxoindolinyl, 2-oxo-2,3-dihydrobenzimidazolyl, 2-oxo-2,3-dihydrobenzoxazolyl or 2-oxo-2,3-dihydrobenzothiazolyl which may optionally bear up to three substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(i) $Q^1$ is 2-oxoindolin-5-yl or 2-oxoindolin-6-yl which bears at the 1-position a substituent selected from methyl, ethyl, propyl, allyl and 2-propynyl; and X, Ar and $Q^2$ have any of the meanings defined hereinbefore or in this section concerning particular compounds of the invention;

(j) $Q^1$ is an 11-membered benzo-fused heterocyclic moiety containing one or two nitrogen heteroatoms, which heterocyclic moiety may optionally bear one oxo or thioxo substituent and up to three further substituents selected from any of those substituents on $Q^1$ defined hereinbefore other than oxo or thioxo; and X, Ar and $Q^2$ have any of the meanings defined hereinbefore or in this section concerning particular compounds of the invention;

(k) $Q^1$ is 1H-benzo[b]azepine or 2,3,4,5-tetrahydro-1H-benzo[b]azepine which may optionally bear one oxo or thioxo substituent and up to three further substituents selected from fluoro, chloro, methyl, ethyl, allyl, 2-propynyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(l) $Q^1$ is 2-oxo-2,3,4,5-tetrahydro-1H-benzo[b]azepine which may optionally bear up to three further substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and X, Ar and $Q^2$ have any of the meanings defined hereinbefore or in this section concerning particular compounds of the invention;

(m) Q is 2-oxo-2,3,4,5-tetrahydro-1H-benzo[b]azepin-7-yl which bears at the 1-position a substituent selected from methyl, ethyl, propyl, allyl and 2-propynyl; and X, Ar and $Q^2$ have any of the meanings defined hereinbefore or in this section concerning particular compounds of the invention;

(n) X is thio, sulphinyl or sulphonyl; and $Q^1$, Ar and $Q^2$ (n), Ar and have any of the meanings defined hereinbefore or in this section concerning particular compounds of the invention;

(o) Ar is phenylene which may optionally bear one or two substituents selected from halogeno, trifluoromethyl, (1–4C)alkyl and (1–4C)alkoxy, Ar is pyridinediyl or pyrimidinediyl which may optionally bear one substituent selected from halogeno, trifluoromethyl and amino, or Ar is thiophenediyl or thiazolediyl; and $Q^1$, X and $Q^2$ have any of the meanings defined hereinbefore or in this section concerning particular compounds of the invention; or (p) Ar is 1,3-phenylene or 5-fluoro-1,3-phenylene; and $Q^1$, X and $Q^2$ have any of the meanings defined hereinbefore or in this section concerning particular compounds of the invention;

(q) Ar is 2,4-thiophenediyl (with the X group in the 2-position) or 2,5-thiophenediyl; and $Q^1$, X and $Q^2$ have any of the meanings defined hereinbefore or in this section concerning particular compounds of the invention;

(r) Ar is 2,4-thiazolediyl (with the X group in the 2-position) or 2,5-thiazolediyl (with the X group in the 2-position); and $Q^1$, X and $Q^2$ have any of the meanings defined hereinbefore or in this section concerning particular compounds of the invention;

(s) $Q^2$ is selected from the groups of the formulae IV and V:

wherein $R^2$ is methyl, ethyl or propyl; and $Q^1$, X and Ar have any of the meanings defined hereinbefore or in this section concerning particular compounds of the invention; or (t) $Q^2$ is a group of the formula IV wherein $R^2$ is methyl, ethyl or propyl; and $Q^1$, X and Ar have any of the meanings defined hereinbefore or in this section concerning particular compounds of the invention.

A preferred compound of the invention comprises an ether derivative of the formula I wherein $Q^1$ is 2-oxo-1,2-dihydroquinolinyl, 2-oxo-1,2,3,4-tetrahydroquinolinyl or 3-oxo-2,3-dihydro-4H-1,4-benzoxazinyl which may optionally bear one, two or three substituents selected from methyl and ethyl;

X is thio, sulphinyl or sulphonyl;

Ar is 1,3-phenylene which may optionally bear one or two fluoro substituents or Ar is 3,5-pyridinediyl, 2-amino-4,6-pyrimidinediyl, 2,4- or 2,5-thiophenediyl or 2,4- or 2,5-thiazolediyl; and $Q^2$ is selected from the groups of the formulae IV and V wherein $R^2$ is methyl or ethyl;

or a pharmaceutically-acceptable salt thereof.

A further preferred compound of the invention comprises an ether derivative of the formula I wherein $Q^1$ is 2-oxoindolinyl, 2-oxo-1,2-dihydroquinolinyl, 2-oxo-1,2,3,4-tetrahydroquinolinyl or 2-oxo-2,3,4,5-tetrahydro-1H-benzo[b]azepinyl which may optionally bear one, two or three substituents selected from fluoro, chloro, methyl, ethyl, allyl and 2-propynyl;

X is thio, sulphinyl or sulphonyl;

Ar is 1,3-phenylene which may optionally bear one or two fluoro substituents or Ar is 2,4- or 2,5-thiophenediyl or 2,4- or 2,5-thiazolediyl; and $Q^2$ is a group of the formula II wherein
  $R^1$ is hydrogen;
  $R^2$ is methyl or ethyl; and
  $R^3$ is hydrogen or methyl;
  or $R^2$ and $R^3$ are linked to form an ethylene group;
or a pharmaceutically-acceptable salt thereof.

A further preferred compound of the invention comprises an ether derivative of the formula I wherein $Q^1$ is 2-oxoindolinyl which may optionally bear one, two or three substituents selected from fluoro, chloro, methyl, ethyl, allyl and 2-propynyl;

X is thio, sulphinyl or sulphonyl;

Ar is 1,3-phenylene which may optionally bear one or two fluoro substituents or Ar is 2,4- or 2,5-thiophenediyl or 2,4- or 2,5-thiazolediyl; and $Q^2$ is a group of the formula II wherein
  $R^1$ is hydrogen;
  $R^2$ is methyl or ethyl; and
  $R^3$ is hydrogen or methyl;
or a pharmaceutically-acceptable salt thereof.

A further preferred compound of the invention comprises an ether derivative of the formula I wherein $Q^1$ is 2-oxo-1,2-dihydroquinolin-6-yl or 2-oxo-1,2,3,4-tetra-hydroquinolin-6-yl which bears at the 1-position a substituent selected from methyl, ethyl and propyl;

X is thio, sulphinyl or sulphonyl;

Ar is 1,3-phenylene or 5-fluoro-1,3-phenylene, or Ar is 2,4-thiophenediyl (with the X group in the 2-position), 2,5-thiophenediyl, 2,4-thiazolediyl (with the X group in the 2-position) or 2,5-thiazolediyl (with the X group in the 2-position); and $Q^2$ is a group of the formula IV wherein $R^2$ is methyl;
or a pharmaceutically-acceptable salt thereof.

A further preferred compound of the invention comprises an ether derivative of the formula I wherein $Q^1$ is 2-oxoindolin-5-yl, 2-oxo-1,2-dihydroquinolin-6-yl, 2-oxo-1,2,3,4-tetrahydroquinolin-6-yl or 2-oxo-2,3,4,5-tetrahydro-1H-benzo[b]azepin-7-yl which optionally bears at the 1-position a substituent selected from methyl, ethyl, allyl and 2-propynyl and which also optionally bears a further substituent selected from fluoro, chloro and methyl;

X is thio, sulphinyl or sulphonyl;

Ar is 1,3-phenylene or 5-fluoro-1,3-phenylene or Ar is 2,4-thiophenediyl (with the X group in the 2-position), 2,5-thiophenediyl, 2,4-thiazolediyl (with the X group in the 2-position) or 2,5-thiazolediyl (with the X group in the 2-position); and $Q^2$ is a group of the formula IV wherein $R^2$ is methyl;
or a pharmaceutically-acceptable salt thereof.

A further preferred compound of the invention comprises an ether derivative of the formula I wherein $Q^1$ is 1-methyl-2-oxo-1,2-dihydroquinolin-6-yl or 1-methyl-2-oxo-1,2,3,4-tetrahydroquinolin-6-yl;

X is thio, sulphinyl or sulphonyl;

Ar is 1,3-phenylene or 5-fluoro-1,3-phenylene, or Ar is 2,4-thiophenediyl (with the X group in the 2-position), 2,5-thiophenediyl, 2,4-thiazolediyl (with the X group in the 2-position) or 2,5-thiazolediyl (with the X group in the 2-position); and $Q^2$ is a group of the formula IV wherein $R^2$ is methyl;
or a pharmaceutically-acceptable salt thereof.

A further preferred compound of the invention comprises an ether derivative of the formula I wherein $Q^1$ is 1-methyl-2-oxo-1,2,3,4-tetrahydroquinolin-6-yl or 1-ethyl-2-oxo-1,2,3,4-tetrahydroquinolin-6-yl;

X is thio, sulphinyl or sulphonyl;

Ar is 2,4-thiazolediyl (with the X group in the 2-position) or 2,5-thiazolediyl (with the X group in the 2-position); and $Q^2$ is a group of the formula IV wherein $R^2$ is methyl;
or a pharmaceutically-acceptable salt thereof.

A further preferred compound of the invention comprises an ether derivative of the formula I wherein $Q^1$ is 1-methyl-2-oxoindolin-5-yl, 1-methyl-2-oxo-1,2-dihydroquinolin-6-yl, 1-allyl-2-oxo-1,2,3,4-tetrahydroquinolin-6-yl, 1-ethyl-2-oxo-1,2,3,4-tetrahydroquinolin-6-yl, 1-methyl-2-oxo-1,2,3,4-tetrahydroquinolin-6-yl, 1-(2-propynyl)-2-oxo-1,2,3,4-tetrahydroquinolin-6-yl, 8-chloro-1-methyl-2-oxo-1,2,3,4-tetrahydroquinolin-6-yl, 7-fluoro-1-methyl-2-oxo-1,2,3,4-tetrahydroquinolin-6-yl, 8-fluoro-1-methyl-2-oxo-1,2,3,4-tetrahydroquinolin-6-yl, 1,8-dimethyl-2-oxo-1,2,3,4-tetrahydroquinolin-6-yl or 1-methyl-2-oxo-2,3,4,5-tetrahydro-1H-benzo[b]azepin-7-yl;

X is thio, sulphinyl or sulphonyl;

Ar is 2,4-thiophenediyl (with the X group in the 2-position), 2,5-thiophenediyl or 2,5-thiazolediyl (with the X group in the 2-position); and $Q^2$ is a group of the formula IV wherein $R^2$ is methyl;
or a pharmaceutically-acceptable salt thereof.

A further preferred compound of the invention comprises an ether derivative of the formula I wherein $Q^1$ is 1-methyl-2-oxo-1,2-dihydroquinolin-6-yl or 1-methyl-2-oxo-1,2,3,4-tetrahydroquinolin-6-yl;

X is thio, sulphinyl or sulphonyl;

Ar is 1,3-phenylene or 5-fluoro-1,3-phenylene; and $Q^2$ is a group of the formula IV wherein $R^2$ is methyl
or a pharmaceutically-acceptable salt thereof.

A further preferred compound of the invention comprises an ether derivative of the formula I wherein $Q^1$ is 1-methyl-2-oxoindolin-5-yl, 1-methyl-2-oxo-1,2-dihydroquinolin-6-yl, 1-allyl-2-oxo-1,2,3,4-tetrahydroquinolin-6-yl, 1-ethyl-2-oxo-1,2,3,4-tetrahydroquinolin-6-yl, 1-methyl-2-oxo-1,2,3,4-tetrahydroquinolin-6-yl, 1-(2-propynyl)-2-oxo-1,2,3,4-tetrahydroquinolin-6-yl, 8-chloro-1-methyl-2-oxo-1,2,3,4-tetrahydroquinolin-6-yl, 7-fluoro-1-methyl-2-oxo-1,2,3,4-tetrahydroquinolin-6-yl, 8-fluoro-1-methyl-2-oxo-1,2,3,4-tetrahydroquinolin-6-yl, 1,8-dimethyl-2-oxo-1,2,3,4-tetrahydroquinolin-6-yl or 1-methyl-2-oxo-2,3,4,5-tetrahydro-1H-benzo[b]azepin-7-yl;

X is thio, sulphinyl or sulphonyl;

Ar is 1,3-phenylene or 5-fluoro-1,3-phenylene; and $Q^2$ is a group of the formula IV wherein $R^2$ is methyl;
or a pharmaceutically-acceptable salt thereof.

A specific especially preferred compound of the invention is the following compound of the formula I, or a pharmaceutically-acceptable salt thereof:

(2S,4R)-4-[5-fluoro-3-(1-methyl-2-oxo-1,2,3,4-tetrahydroquinolin-6-ylthio)phenyl]-4-hydroxy-2-methyltetrahydropyran or (2S,4R)-4-[5-fluoro-3-(1-methyl-2-oxo-1,2,3,4-tetrahydroquinolin-6 -ylsulphonyl)phenyl]-4-hydroxy-2-methyltetrahydropyran.

A further specific especially preferred compound of the invention is the following compound of the formula I, or a pharmaceutically-acceptable salt thereof:

(2S,4R)-4-hydroxy-2-methyl-4-[2-(1-methyl-2-oxo-1,2,3,4 -tetrahydroquinolin-6-ylthio)thiazol-5-yl]tetrahydropyran, (2S,4R)-4-hydroxy-2-methyl-4-[2-(1-methyl-2-oxo-1,2,3,4 -tetrahydroquinolin-6-ylsulphonyl)thiazol-5-yl]tetrahydropyran, (2S,4R)-4-[2-(7-fluoro-1-methyl-2-oxo-1,2,3,4-tetrahydroquinolin-6 -ylthio)thiazol-5-yl]-4-hydroxy-2-methyltetrahydropyran or (2S,4R)-4-hydroxy-2-methyl-4-[2-(1-methyl-2-oxoindolin-5 -ylthio)thiazol-5-yl]tetrahydropyran.

A further specific especially preferred compound of the invention is the following compound of the formula I, or a pharmaceutically-acceptable salt thereof:

(2S,4R)-4-hydroxy-2-methyl-4-[2-(1-methyl-2-oxo-1,2,3,4 -tetrahydroquinolin-6-ylthio)thien-4-yl]tetrahydropyran, (2S,4R)-4-hydroxy-2-methyl-4-[2-(1-methyl-2-oxo-1,2,3,4 -tetrahydroquinolin-6-ylsulphonyl)thien-4-yl]tetrahydropyran, (2S,4R)-4-hydroxy-2-methyl-4-[2-(1-methyl-2-oxo-1,2,3,4 -tetrahydroquinolin-6-ylthio)thien-5-yl]tetrahydropyran, (2S,4R)-4-hydroxy-2-methyl-4-[2-(1-methyl-2-oxo-1,2 -dihydroquinolin-ylthio)thien-4-yl]tetrahydropyran, (2S,4R)-4-hydroxy-2-methyl-4-[2-(1,8-dimethyl-2-oxo-1,2,3,4 -tetrahydroquinolin-6-ylthio)thien-4-yl]tetrahydropyran, 4-[2-(8-fluoro-1-methyl-2-oxo-1,2,3,4-tetrahydroquinolin-6 -ylthio)thien-4-yl]-4-hydroxy-2-methyltetrahydropyran, 4-[2-(7-fluoro-1-methyl-2-oxo-1,2,3,4-tetrahydroquinolin-6 -ylthio)thien-4-yl]-4-hydroxy-2-methyltetrahydropyran or (2S,4R)-4-hydroxy-2-methyl-4-[2-(1-methyl-2-oxoindolin-5 -ylthio)thien-yl]tetrahydropyran.

A further specific especially preferred compound of the invention is the following compound of the formula I, or a pharmaceutically-acceptable salt thereof:

(2S,4R)-4-hydroxy-2-methyl-4-[3-(1-methyl-2-oxo-1,2,3,4 -tetrahydroquinolin-6-ylthio)phenyl]tetrahydropyran, (2S,4R)-4-hydroxy-2-methyl-4-[3-(1-methyl-2-oxo-1,2,3,4 -tetrahydroquinolin-6-ylsulphonyl)phenyl]tetrahydropyran, (2S,4R)-4-[3-(1-ethyl-2-oxo-1,2,3,4-tetrahydroquinolin-6-ylthio)phenyl]-4-hydroxy-2-methyltetrahydropyran, (2S,4R)-4-[3-(7-fluoro-1-methyl-2-oxo-1,2,3,4-tetrahydroquinolin-6 -ylthio)phenyl]-4-hydroxy-2-methyltetrahydropyran, (2S,4R)-4-[3-(1-methyl-2-oxo-1,2-dihydroquinolin-6 -ylthio)phenyl]tetrahydropyran, (2S,4R)-4-[3-(8-chloro-1-methyl-2-oxo-1,2,3,4-tetrahydroquinolin-6ylthio)phenyl]-4-hydroxy-2-methyltetrahydropyran or (2S,4R)-4-hydroxy-2-methyl-4-[3-(1-methyl-2-oxoindolin-5-ylthio)phenyl]tetrahydropyran.

In a further aspect of the invention we have discovered that certain compounds of the invention lack to a substantial degree the undesirable property of auto-induction. This has, for example, been established for compounds such as those disclosed within Examples 3, 9 and 28. Such compounds are of particular value in the treatment of various leukotriene-dependent diseases such as inflammatory and/or allergic diseases in warm-blooded animals as they lack the disadvantages which may arise as a result of auto-induction. Thus, for example, the assessment of pharmacological and toxicological data is made more complex if the test compound has been shown to possess a significant degree of auto-induction. In addition auto-induction may foreshadow the general induction of enzymes which could have disadvantageous effects such as a detrimental increase in the rate of metabolism of any co-administered drugs.

In another aspect of the invention we have discovered that certain compounds of the invention are crystalline. The crystalline compounds of the invention are those for which a melting point has been given within the Examples provided hereinafter, for example the compounds of Examples 27 and 28. Thus such compounds are of value when their preparation on a larger scale is required. The purification, analysis and handling of a material is facilitated if it is formed in the crystalline state. It is known, for example, that the removal of solvent residues from non-crystalline, oily materials is problematical. In addition the preparation of a pharmaceutical composition comprising a crystalline material is a conventional procedure. The composition may, for example, be in a form suitable for oral use such as a tablet or capsule; or, for example, in a form suitable for administration by inhalation, for example as a finely divided powder or a microcrystalline form. Such options for the formulation of the material are precluded should it be formed in an oily state.

A compound of the invention comprising an ether derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Q^1$, X, Ar and $Q^2$ have any of the meanings defined hereinbefore, provided that when there is an amino, alkylamino or hydroxy group in $Q^1$, Ar or $Q^2$ then any such group may optionally be protected by a conventional protecting group which may be removed when so desired by conventional means.

(a) The coupling, conveniently in the presence of a suitable base, of a compound of the formula $Q^1$—X—H with a compound of the formula Z—Ar—$Q^2$ wherein Z is a displaceable group.

A suitable displaceable group Z is, for example, a halogeno or sulphonyloxy group, for example a fluoro, chloro, bromo, iodo, methanesulphonyloxy or toluene-4-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, potassium butoxide, lithium hydroxide, sodium hydroxide, potassium hydroxide, sodium hydride or potassium hydride, or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon.

A suitable protecting group for a hydroxy group is, for example, an acyl group, for example a (2–4C)alkanoyl group (especially acetyl), an aroyl group (especially benzoyl), an arylmethyl group (especially benzyl), a tri-(1–4C)alkylsilyl group (especially trimethylsilyl or tert-butyldimethylsilyl) or an aryldi-(1–4C)alkylsilyl group (especially dimethylphenylsilyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride.

The starting materials of the formula $Q^1$—X—H and of the formula Z—Ar—$Q^2$ may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist. The disclosures of European Patent Applications Nos. 385662, 0420511, 0462812 and 0462813 are particularly relevant to the preparation of suitable starting materials.

(b) The coupling, conveniently in the presence of a suitable base as defined hereinbefore, of a compound of the formula $Q^1$—Z, wherein Z is a displaceable group as defined hereinbefore, with a compound of the formula H—X—Ar—$Q^2$.

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula $Q^1$-Z and of the formula H—X—Ar—$Q^2$ may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist. The disclosures of European Patent Applications Nos. 0385662, 0420511, 0462812 and 0462813 are particularly relevant to the preparation of suitable starting materials.

(c) The coupling of a compound of the formula $Q^1$—X—Z, wherein Z is a displaceable group as defined hereinbefore or, when X is a thio group, Z may be a group of the formula $Q^1$—X—, with an organometallic reagent of the formula M—Ar—$Q^2$, wherein M is an alkali metal or alkaline earth metal such as lithium or calcium or M represents the magnesium halide portion of a conventional Grignard reagent.

The coupling reaction is conveniently performed in a suitable inert solvent or diluent as defined hereinbefore and at a temperature in the range, for example, −80° to +50° C., conveniently in the range −80° C. to ambient temperature.

The preparation of the starting materials of the formula $Q^1$—X—Z and of the formula M—Ar—$Q^2$ may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist. The disclosures of the European Patent Applications set out hereinbefore are particularly relevant to the preparation of suitable starting materials.

(d) For the production of those compounds of the formula I wherein X is a sulphinyl or sulphonyl group, the oxidation of a compound of the formula I wherein X is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein the $R^1$ group within $Q^2$ is a (2–5C)alkanoyl or benzoyl group, the acylation of a compound of the formula I wherein the $R^1$ group within $Q^2$ is hydrogen.

A suitable acylating agent is, for example, any agent known in the art for the acylation of an alcohol to an ester, for example an acyl halide, for example a (2–5C)alkanoyl chloride or bromide or a benzoyl chloride or bromide, in the presence of a suitable base as defined hereinbefore, an alkanoic acid anhydride, for example a (2–5C)alkanoic acid anhydride, or an alkanoic acid mixed anhydride, for example the mixed anhydride formed by the reaction of an alkanoic acid and a (1–4C)alkoxycarbonyl halide, for example a (1–4C)alkoxycarbonyl chloride, in the presence of a suitable base. In general the reaction is carried out in a suitable solvent or diluent such as methylene chloride, acetone, tetrahydrofuran, tert-butyl methyl ether or glacial acetic acid and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $Q^1$ bears an alkyl or substituted alkyl substituent on an available nitrogen atom, the alkylation of a compound of the formula I wherein $Q^1$ bears a hydrogen atom on said available nitrogen atom.

A suitable alkylating agent is, for example, any agent known in the art for the alkylation of an available nitrogen atom, for example an alkyl or substituted alkyl halide, for example a (1–4C)alkyl chloride, bromide or iodide or a substituted (1–4C)alkyl chloride, bromide or iodide, in the presence of a suitable base as defined hereinbefore. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

(g) For the production of those compounds of the formula I wherein $Q^1$ bears one or two thioxo substituents, the reaction of a compound of the formula I wherein $Q^1$ bears one or two oxo substituents with a thiation reagent such that each oxo substituent is converted into a thioxo substituent.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-L0. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-L0 by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane B2($TxB_2$) described by Carey and Forder (see above). This test provides an indication of the effects of a test compound against 5-L0 and also cyclooxygenase in the presence of blood cells and proteins. It permits the selectivity of the inhibitory effect on 5-L0 or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-L0 or cyclooxygenase.

c) An in vivo system involving measuring the effects of a test compound administered orally to a group of male rats against the liberation of $LTB_4$ induced by zymosan within an air pouch generated within the subcutaneous tissue of the back of the rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-L0 in an inflammatory milieu.

Although the pharmacological properties of the compounds of the formula I vary with structural changes as expected, in general compounds of the formula I possess 5-L0 inhibitory effects at the following concentrations or doses in at least one of the above tests a)–c):

Test a): $IC_{50}$ ($LTB_4$) in the range, for example, 0.01–40 µM $IC_{50}$ ($TxB_2$) in the range, for example, 40–200 µM;

Test b): oral $ED_{50}$($LTB_4$) in the range, for example, 0.1–100 mg/kg;

Test c): oral $ED_{50}$($LTB_4$) in the range, for example, 0.1–100 mg/kg.

No overt toxicity or other untoward effects are present in tests b) and/or c) when compounds of the formula I are administered at several multiples of their minimum inhibitory dose or concentration.

Thus, by way of example, the compound (2S,4R)-4-[5-fluoro-3(1-methyl-2-oxo-1,2,3,4-tetrahydroquinolin-6-yl-sulphonyl)phenyl]-4-hydroxy-2-methyltetrahydropyran has an $IC_{50}$ of 0.03 µM against $LTB_4$ in test a) and an $ED_{50}$ of approximately 0.15 mg/kg against $LTB_4$ in test c); the compound (2S,4R)-4-hydroxy-2-methyl-4-[2-(1-methyl-2-oxo1,2,3,4-tetrahydroquinolin-6-ylthio)thien-4-yl]tetrahydropyran has an $IC_{50}$ of 0.03 μM against $LTB_4$ in test a) and an $ED_{50}$ of approximately 0.02 mg/kg against $LTB_4$ in test c); the compound (2S,4R)-4-hydroxy- 2-methyl-4-[2-(1-methyl-2-oxoindolin-5-ylthio)thien-4-yl]tetrahydropyran has an $IC_{50}$ of 0.02 μM against $LTB_4$ in test a) and an $ED_{50}$ of approximately 0.05 mg/kg against $LTB_4$ in test c); and the compound (2S,4R)-4-hydroxy-2-methyl-4-[2-(1-methyl-2-oxo-1,2,3,4-tetrahydro- quinolin-6-ylthio)thiazol-5-yl]tetrahydropyran has an $IC_{50}$ of 0.05 μM against $LTB_4$ in test a) and an $ED_{50}$ of approximately 0.2 mg/kg against $LTB_4$ in test c).

These compounds are examples of compounds of the invention which show selective inhibitory properties for 5-L0 as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an ether derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an ether derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an ether derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those diseases such as allergic and inflammatory conditions and disorders of bone metabolism which are due alone or in part to the effects of the metabolites of arachidonic acid arising by the linear (5-L0 catalysed) pathway and in particular the leukotrienes, the production of which is mediated by 5-L0. As previously mentioned, such conditions include, for example, asthmatic conditions, allergic reactions, allergic rhinitis, allergic shock, psoriasis, atopic dermatitis, cardiovascular and cerebrovascular disorders, arthritic and inflammatory joint disease, inflammatory bowel diseases, conjunctivitis, the conditions of shock or trauma and various disorders of bone metabolism.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-L0. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-L0 inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an ether derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the formula I have satisfactory microanalyses and their structures were confirmed by nuclear magnetic resonance (NMR) and mass spectral techniques; unless otherwise stated, $CDCl_3$ solutions of the end-products of the formula I were used for the determination of NMR spectral data, chemical shift values were measured on the delta scale; the following abbreviations have been used: s, singlet; d, doublet; t, triplet; q, quartet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviation has been used:

| NMP | N-methylpyrrolidin-2-one; |
|---|---|
| DMF | N,N-dimethylformamide; |
| THF | tetrahydrofuran; |
| DMSO | dimethyl sulphoxide. |

EXAMPLE 1

A mixture of 6-mercapto-1-methyl-1,2,3,4-tetrahydroquinolin- one (0.19 g), (2S,4R)-4-(3,5-difluorophenyl)-4-hydroxy-2-methyltetrahydropyran (0.23 g), lithium hydroxide monohydrate (0.05 g) and NMP (1 ml) was stirred and heated to 130° C. for 6 hours. The mixture was cooled to ambient temperature and partitioned between diethyl ether and water. The organic phase was washed with water, dried ($MgSO_4$) and evaporated. The residue was purified by column chromatography using increasingly polar mixtures of hexane and ethyl acetate as eluent. There was thus obtained (2S,4R)-4-[5-fluoro-3-(1-methyl-2-oxo-1,2,3,4 -tetrahydroquinolin-6-ylthio)phenyl]-4-hydroxy- 2-methyltetrahydropyran (0.065 g, 16%), m.p. 181°–183° C. (recrystallised from methanol).

NMR Spectrum: 1.2 (d, 3H), 1.5–1.75 (m, 3H), 2.05 (m, 1H), 2.65 (m, 2H), 2.9 (m, 2H), 3.38 (s, 3H), 3.85–4.0 (m, 3H), 6.7 (m, 1H), 7.0 (m, 1H), 7.2 (m, 1H), 7.28 (m, 1H), 7.36 (m, 1H).

The 6-mercapto-1-methyl-1,2,3,4-tetrahydroquinolin-2-one used as a starting material was obtained as follows:

A mixture of concentrated hydrochloric acid (5 drops) and water (50 ml) was added to a stirred mixture of di-(1-methyl-2-oxo-1,2,3,4-tetrahydroquinolin-6-yl) disulphide (European Patent Application No. 0462812, Example 7 thereof; 38.4 g), triphenylphosphine (29 g) and 1,4-dioxan (300 ml). The mixture was stirred at ambient temperature for 30 minutes. The mixture was concentrated by evaporation to reduce the volume by approximately one half. The residue was partitioned between ethyl acetate and 0.5N aqueous sodium hydroxide solution. The aqueous phase was washed with diethyl ether and then acidified to $pH_2$ by the addition of dilute aqueous hydrochloric acid. The acidic mixture was extracted with ethyl acetate. The organic phase was dried ($MgSO_4$) and evaporated. The residual oil was dissolved in diethyl ether and hexane was added. There was thus obtained 6-mercapto-1-methyl-1,2,3,4-tetrahydroquinolin-2-one as a solid (35.5 g, 92%) which was used without further purification.

The (2S,4R)-4-(3,5-difluorophenyl)-4-hydroxy-2-methyltetrahydropyran used as a starting material was obtained as follows:

Using an analogous procedure to that described in the first paragraph of the portion of Example 9 of European Patent Application No. 0462813 which is concerned with the preparation of starting materials, the Grignard reagent obtained from 3,5-difluorobromobenzene was reacted with (2S)-2-methyltetrahydropyran-4-one (European Patent Application No. 0385662, Example 20 thereof) to give (2S,4R)-4-(3,5- difluorophenyl)-4-hydroxy-2-methyltetrahydropyran in 25% yield as an oil.

EXAMPLE 2

A mixture of (2S,4R)-4-[5-fluoro-3-(1-methyl-2-oxo-1,2, 3,4 -tetrahydroquinolin-6-ylthio)phenyl]-4-hydroxy-2-methyltetrahydropyran (0.095 g), potassium peroxymonosulphate (0.22 g), ethanol (2 ml) and water (2 ml) was stirred at ambient temperature for 18 hours. The mixture was partitioned between ethyl acetate and water. The organic phase was dried ($MgSO_4$) and evaporated. The residue was purified by column chromatography using increasingly polar mixtures of methylene chloride and ethyl acetate as eluent. There was thus obtained (2S,4R)-4-[5-fluoro-3-(1-methyl-2-oxo-1,2,3,4-tetrahydroquinolin-6 -ylsulphonyl)phenyl]-4-hydroxy-2-methyltetrahydropyran (0.06 g, 58%), m.p. 151°–154° C. (recrystallised from a mixture of hexane and ethyl acetate).

NMR Spectrum: 1.22 (d, 3H), 1.55–1.80 (m, 3H), 2.08 (m, 1H), 2.69 (m, 2H), 2.97 (m, 2H), 3.36 (s, 3H), 3.85–4.0 (m, 3H), 7.07 (m, 1H), 7.4 (m, 1H), 7.5 (m, 1H), 7.72 (m, 1H), 7.8–7.9 (m, 2H).

EXAMPLE 3

6-Mercapto-1-methyl-1,2,3,4-tetrahydroquinolin-2-one (0.052 g) was added to a mixture of (2S,4R)-4-(2-chlorothiazol-5-yl)-4 -hydroxy-2-methyltetrahydropyran (0.062 g), potassium carbonate (0.04 g) and NMP (2 ml). The mixture was stirred and heated to 100° C. for 90 minutes. The mixture was cooled to ambient temperature and partitioned between ethyl acetate and water. The organic phase was washed with brine, dried ($MgSO_4$) and evaporated. The residue was purified by column chromatography using a 1:3 mixture of petroleum ether (b.p. 40°–60° C.) and ethyl acetate as eluent. There was thus obtained (2S,4R)-4-hydroxy-2-methyl-4-[2-(1-methyl-2-oxo-1,2,3,4-tetrahydroquinolin-6-ylthio)thiazol-5-yl]tetrahydropyran (0.064 g, 62%) as a foam;

NMR Spectrum: 1.17 (d, 3H), 1.6–1.9 (m, 4H), 2.05 (m, 1H), 2.7 (m, 2H), 2.95 (m, 2H), 3.4 (s, 3H), 3.9 (m, 3H), 7.05 (d, 1H), 7.45 (d, 1H), 7.5 (s, 1H), 7.55 (m, 1H).

The (2S,4R)-4-(2-chlorothiazol-5-yl)-4-hydroxy-2-methyltetrahydropyran used as a starting material was obtained as follows:

A saturated aqueous solution of sodium nitrite (6.9 g) was added dropwise to a stirred solution of 2-aminothiazole (10 g) in concentrated hydrochloric acid (50 ml) which had been cooled to 0° C. The mixture was stirred at 0° C. for 75 minutes. Cuprous chloride (9.9 g) was added portionwise, the reaction temperature being maintained at 0° C., and the mixture was stirred for 2.5 hours. The mixture was neutralised by the addition of 10N aqueous sodium hydroxide solution. The mixture was partitioned between diethyl ether and water. The organic phase was washed with brine, dried (MgSO4) and evaporated. The residue was purified by distillation. There was thus obtained 2-chlorothiazole (3.95 g, b.p. 68° C. at 68 mm of mercury).

A solution of 2-chlorothiazole (0.5 g) in diethyl ether (4 ml) and n-butyl-lithium (2.5M in hexane, 1.8 ml) were added simultaneously during 10 minutes to diethyl ether (5 ml) which had been cooled to −78° C. The mixture was stirred for 3.5 hours and allowed to warm to −20° C. The mixture was recooled to -78° C. and a solution of (2S)-2-methyltetrahydropyran-4-one [European Patent Application No. 0385662 (Example 20 thereof); 0.43 g] in diethyl ether (4 ml) was added. The mixture was stirred and allowed to warm to −10° C. A 5% aqueous solution of ammonium chloride was added and the mixture was extracted with diethyl ether. The organic phase was washed with brine, dried (MgSO$_4$) and evaporated. The residue was purified by column chromatography using a 1:1 mixture of petroleum ether (b.p. 40°–60° C.) and ethyl acetate as eluent. There was thus obtained (2S,4R)-4-(2- chlorothiazol-5-yl)-4-hydroxy-2-methyltetrahydropyran (0.11 g, 13%) as an oil.

EXAMPLE 4

3-Chloroperoxybenzoic acid (0.493 g) was added to a stirred solution of (2S,4R)-4-hydroxy-2-methyl-4-[2-(1-methyl-2-oxo-1,2,3,4 -tetrahydroquinolin-6-ylthio)thiazol-5-yl]tetrahydropyran (0.28 g) in methylene chloride (5 ml) which had been cooled to 0° C. The mixture was allowed to warm to ambient temperature and was stirred for 16 hours. A saturated aqueous sodium bicarbonate solution was added and the mixture was extracted with diethyl ether. The organic phase was washed with brine, dried (MgSO$_4$) and evaporated. The residue was purified by column chromatography using a 1:4 mixture of petroleum ether (b.p. 40°–60° C.) and ethyl acetate as eluent. There was thus obtained (2S,4R)-4-hydroxy-2-methyl-4-[2-(1-methyl-2-oxo-1,2,3,4 -tetrahydroquinolin-6-ylsulphonyl)thiazol-5-yl] tetrahydropyran (0.22 g, 72%) as an oil;

NMR Spectrum: 1.20–1.22 (d, 3H), 1.69–1.75 (m, 1H), 1.80–1.84 (m, 1H), 1.88–1.94 (m, 1H), 2.06–2.09 (m, 1H), 2.31 (s, 1H), 2.67–2.71 (m, 2H), 2.97–3.01 (m, 2H), 3.37 (s, 3H), 3.87–3.95 (m, 3H), 7.10–7.12 (d, 1H), 7.75 (s, 1H), 7.86–7.88 (m, 1H), 7.96–7.99 (m, 1H).

EXAMPLE 5

A mixture of 6-iodo-1-methyl-1,2,3,4-tetrahydroquinolin-2-one (1.15 g), (2S,4R)-4-hydroxy-4-(2-mercaptothien-4-yl)-2-methyltetrahydropyran (0.92 g), cuprous chloride (0.12 g), potassium carbonate (1.66 g) and DMF (40 ml) was stirred and heated to 130° C. for 2 hours. The mixture was cooled to ambient temperature and partitioned between ethyl acetate and water. The organic phase was washed with water and with brine, dried (MgSO4) and evaporated. The residue was purified by column chromatography using increasingly polar mixtures of hexane and ethyl acetate as eluent. There was thus obtained (2S,4R)-4-hydroxy-2 -methyl-4-[2-(1-methyl-2-oxo-1,2,3,4-tetrahydroquinolin-6 -ylthio)thien-4-yl]tetrahydropyran as a foam (0.6 g);

NMR Spectrum: 1.2 (d, 3H), 1.7 (m, 3H), 2.1 (m, 1H), 2.6 (m, 2H), 2.9 (m, 2H), 3.3 (s, 3H), 3.9 (m, 3H), 6.9 (d, 1H), 7.2 (m, 4H).

The 6-iodo-1-methyl-1,2,3,4-tetrahydroquinolin-2-one used as a starting material was obtained as follows:

A mixture of 1-methyl-2-oxo-1,2-dihydroquinolin-2-one (European Patent Application No. 0420511, Example 1 thereof; 8 g), 10% palladium-on-charcoal catalyst (2 g) and ethanol (60 ml) was stirred under a pressure of 3.5 atmospheres of hydrogen for 24 hours. The mixture was filtered and evaporated. The residue was purified by column chromatography using a 9:1 mixture of methylene chloride and diethyl ether as eluent. There was thus obtained 1-methyl-2-oxo-1,2,3,4-tetrahydroquinolin-2-one (7.88 g, 98%) as an oil.

A mixture of a portion (1.2 g) of the product so obtained, iodine monochloride (1.9 g) and glacial acetic acid (25 ml) was stirred and heated to 80° C. for 2 hours. The mixture was cooled to ambient temperature and poured into a dilute aqueous sodium thiosulphate solution. The mixture was neutralised by the addition of sodium bicarbonate and extracted with ethyl acetate. The organic phase was washed with water, with a saturated aqueous sodium bicarbonate solution and with brine, dried (MgSO$_4$) and evaporated. The residue was recrystallised from a mixture of hexane and ethyl acetate. There was thus obtained 6-iodo-1-methyl-1, 2,3,4-tetrahydroquinolin- 2-one (1.09 g, 51%); NMR Spectrum: (CD$_3$SOCD$_3$) 2.65 (t, 2H), 2.85 (t, 2H), 3.2 (s, 3H), 6.9 (d, 1H), 7.6 (m, 2H).

The (2S,4R)-4-hydroxy-4-(2-mercaptothien-4-yl)-2-methyltetrahydropyran used as a starting material was obtained as follows:

n-Butyl-lithium (1.6M in hexane, 28.2 ml) was added to a stirred mixture of 2,4-dibromothiophene (*J. Org. Chem.*, 1988, 53, 417; 10 g) and diethyl ether (150 ml) which had been cooled to −75° C. The mixture was stirred at −75° C. for 1 hour. A solution of dimethyl disulphide (3.1 g) in diethyl ether (10 ml) was added and the mixture was allowed to warm to −20° C. during 1 hour. The mixture was poured into water. The organic phase was washed with water and with brine, dried (MgSO$_4$) and evaporated. There was thus obtained 4-bromo-2-methylthiothiophene (8.9 g).

n-Butyl-lithium (1.6M in hexane, 14.7 ml) was added to a stirred solution of a portion (4.9 g) of the material so obtained in diethyl ether (70 ml) which had been cooled to −70° C. The mixture was stirred at −70° C. for 30 minutes. A solution of (2S)-2 -methyltetrahydropyran-4-one (2 g) in diethyl ether (5 ml) was added. The mixture was stirred at −70° C. for 30 minutes and then allowed to warm to ambient temperature. The mixture was poured into water. The organic phase was washed with water and with brine, dried (MgSO$_4$) and evaporated. The residue was purified by column chromatography using increasingly polar mixtures of hexane and ethyl acetate as eluent. There was thus obtained (2S,4R}-4-hydroxy-2-methyl-4-(2-methylthiothien-4-yl)tetrahydropyran (0.65 g);

NMR Spectrum: 1.2 (d, 3H), 1.7 (m, 3H), 2.0 (m, 2H), 2.5 (s, 3H), 3.9 (m, 3H), 7.1 (m, 2H), and (2S,4S)-4-hydroxy-2-methyl-4-(2-methylthiothien-4-yl)tetrahydropyran (2.45 g);

NMR Spectrum: (CDCl₃+D20) 1.2 (d, 3H), 1.65 (m, 1H), 1.95 (m, 1H), 2.2 (m, 2H), 2.5 (s, 3H), 3.4 (m, 2H), 3.95 (m, 1H), 7.1 (m, 2H).

After repetition of the preceding reaction, a mixture of the product so obtained (1.1 g), sodium methanethiolate (0.42 g) and DMF (20 ml) was stirred and heated to 130° C. for 90 minutes. The mixture was cooled to ambient temperature and partitioned between ethyl acetate and water. The organic phase was washed with water and with brine, dried (MgSO₄) and evaporated. There was thus obtained (2S,4R)-4-hydroxy-4-(2-mercaptothien-4-yl)-2-methyltetrahydropyran as a liquid (0.92 g) which was used without further purification.

EXAMPLE 6

A mixture of 6-mercapto-1-methyl-1,2,3,4-tetrahydroquinolin-2-one (0.23 g), (2S,4R)-4-hydroxy-4-(3-iodophenyl)-2-methyltetrahydropyran (0.35 g), potassium carbonate (0.2 g), cuprous chloride (0.05 g) and DMF (3 ml) was stirred and heated to 120° C. for 2 hours. The mixture was cooled to ambient temperature and partitioned between ethyl acetate and water. The organic phase was dried (Na₂SO₄) and evaporated. The residue was purified by column chromatography using increasingly polar mixtures of hexane and ethyl acetate as eluent. There was thus obtained (2S,4R)-4-hydroxy-2-methyl-4-[3-(1-methyl-2-oxo-1,2,3,4-tetrahydroquinolin-6-ylthio)phenyl]tetrahydropyran (0.33 g), m.p. 135°–137° C. (recrystallised from a mixture of hexane and ethyl acetate);

NMR Spectrum: 1.21 (d, 3H), 1.55–1.8 (m, 4H), 2.1 (m, 1H), 2.66 (m, 2H), 2.86 (m, 2H), 3.35 (s, 3H), 3.85–4.05 (m, 3H), 6.93 (d, 1H), 7.13 (m, 1H), 7.2–7.4 (m, 4H), 7.47 (m, 1H).

The (2S,4R)-4-hydroxy-4-(3-iodophenyl)-2-methyltetrahydropyran used as a starting material was obtained as follows:

n-Butyl-lithium (1.5M in hexane, 40 ml) was added dropwise to a stirred solution of 1,3-diiodobenzene (19.8 g) in THF (200 ml) which had been cooled to −70° C. The mixture was stirred at −70° C. for 12 minutes. (2S)-2-Methyltetrahydropyran-4-one (5.7 g) was added. The mixture was stirred, allowed to warm to ambient temperature and stirred at ambient temperature for 1 hour. The mixture was acidified by the addition of glacial acetic acid and partitioned between diethyl ether and water. The organic phase was washed with brine, dried (Na₂SO₄) and evaporated. A solution of the residue in diethyl ether (50 ml) was added to concentrated sulphuric acid (35% v/v, 200 ml) which had been cooled to 0° C. The mixture was stirred and allowed to warm to ambient temperature. The mixture was stirred at ambient temperature for 3 hours. The mixture was poured onto crushed ice and extracted with diethyl ether. The organic phase was washed with water, with a saturated aqueous sodium bicarbonate solution and with brine, dried (Na₂SO₄) and evaporated. The residue was purified by column chromatography using increasingly polar mixtures of hexane and ethyl acetate as eluent. There was thus obtained (2S,4R)-4-hydroxy-4-(3-iodophenyl)-2-methyltetrahydropyran (12 g, 75%).

EXAMPLE 7

Using an analogous procedure to that described in Example 2, (2S,4R)-4-hydroxy-2-methyl-4-[3-(1-methyl-2-oxo-1,2,3,4-tetrahydroquinolin-6-ylthio)phenyl]tetrahydropyran was oxidised to give (2S,4R)-4-hydroxy-2-methyl-4-[3-(1-methyl-2-oxo-1,2,3,4-tetrahydroquinolin-6-ylsulphonyl)phenyl]tetrahydropyran in 82% yield;

NMR Spectrum: 1.22 (d, 3H), 1.5–1.95 (m, 4H), 2.1 (m, 1H), 2.66 (m, 2H), 2.96 (m, 2H), 3.35 (s, 3H), 3.85–4.05 (m, 3H), 7.06 (m, 1H), 7.50 (m, 1H), 7.65–7.75 (m, 2H), 7.8–7.9 (m, 2H).

EXAMPLE 8

Using an analogous procedure to that described in Example 6, 1-ethyl-6-mercapto-1,2,3,4-tetrahydroquinolin-2-one was reacted with (2S,4R)-4-hydroxy-4-(3-iodophenyl)-2-methyltetrahydropyran to give (2S,4R)-4-[3-(1-ethyl-2-oxo-1,2,3,4-tetrahydroquinolin-6-ylthio)phenyl]-4-hydroxy-2-methyltetrahydropyran in 55% yield, m.p. 148°–149° C. (recrystallised from diethyl ether);

NMR Spectrum: 1.15–1.3 (m, 6H), 1.55–1.8 (m, 4H), 2.1 (m, 1H), 2.65 (m, 2H), 2.85 (m, 2H), 3.85–4.05 (m, 5H), 6.96 (d, 1H), 7.12 (m, 1H), 7.2–7.4 (m, 4H), 7.48 (m, 1H).

The 1-ethyl-6-mercapto-1,2,3,4-tetrahydroquinolin-2-one used as a starting material was obtained as follows:

A mixture of 2-hydroxyquinoline (12 g), 10% palladium-on-charcoal catalyst (5 g) and ethanol (150 ml) was stirred under 5 atmospheres pressure of hydrogen for 36 hours. The mixture was filtered and evaporated. There was thus obtained 1,2,3,4-tetrahydroquinolin-2-one (9.0 g), m.p. 156–158° C.

Sodium hydride (50% dispersion in mineral oil, 0.23 g) was added to a stirred mixture of 1,2,3,4-tetrahydroquinolin-2-one (0.64 g), ethyl iodide (1.7 ml) and DMF (5 ml) which had been cooled to 0° C. The mixture was allowed to warm to ambient temperature and was stirred for 90 minutes. The mixture was acidified by the addition of glacial acetic acid. The mixture was partitioned between diethyl ether and water. The organic phase was washed with brine, dried (Na₂SO₄) and evaporated. The residue was purified by column chromatography using increasingly polar mixtures of hexane and ethyl acetate as eluent. There was thus obtained 1-ethyl-1,2,3,4-tetrahydroquinolin-2-one as an oil (0.7 g, 91%).

A mixture of the material so obtained and chlorosulphonic acid (1.2 ml) was stirred and heated to 60° C. for 1 hour. The mixture was poured onto crushed ice and extracted with methylene chloride. The organic phase was dried (Na₂SO₄) and evaporated. There was thus obtained 1-ethyl-2-oxo-1,2,3,4-tetrahydroquinolin-6-ylsulphonyl chloride (0.7 g, 70%) which was used without further purification.

A mixture of the material so obtained, trimethylsilyl chloride (2.27 ml), potassium iodide (3.4 g) and acetonitrile (20 ml) was stirred at ambient temperature for 72 hours. Water (200 ml) was added and the mixture was basified to pH₈ by the addition of potassium carbonate. Sodium metabisulphite was added portionwise to remove the brown colouration resulting from the presence of iodine. The mixture was extracted with ethyl acetate. The organic phase was dried (Na₂SO₄) and evaporated. There was thus obtained di-(1-ethyl-2-oxo-1,2,3,4-tetrahydroquinolin-6-yl) disulphide as a gum (0.52 g) which was used without further purification.

Using an analogous procedure to that described in the first paragraph of the portion of Example 1 which is concerned with the preparation of starting materials, di-(1-ethyl-2-oxo-1,2,3,4-tetrahydroquinolin-6-yl) disulphide was reduced to give 1-ethyl-6-mercapto1,2,3,4-tetrahydroquinolin-2-one as a gum in 70% yield.

EXAMPLE 9

Using an analogous procedure to that described in Example 4, (2S,4R)-4-hydroxy-2-methyl-4-[2-(1-methyl-2-oxo-1,2,3,4 -tetrahydroquinolin-6-ylthio)thien-4-yl]tetrahydropyran was oxidised to give (2S,4R)-4-hydroxy-2-methyl-4-[2-(1-methyl-2-oxo-1,2,3,4 -tetrahydroquinolin-6-ylsulphonyl)thien-4-yl]tetrahydropyran in 52% yield, m.p. 64°–66° C., and after recrystallisation from a 50:1 mixture of diethyl ether and methylene chloride, m.p. 110° C.;

NMR Spectrum: 1.2 (d, 3H), 1.6–1.82 (m, 3H), 1.96–2.05 (m, 1H), 2.68 (m, 2H), 2.96 (m, 2H), 3.36 (s, 3H), 3.83–3.91 (m, 3H), 7.07 (d, 1H), 7.51 (s, 1H), 7.70 (s, 1H), 7.76 (m, 1H), 7.88 (m, 1H).

EXAMPLE 10

Using an analogous procedure to that described in Example 6, 6-mercapto-1,2,3,4-tetrahydroquinolin-2-one was reacted with (2S,4R)-4-hydroxy-4-(3-iodophenyl)-2-methyltetrahydropyran to give (2S,4R)-4-hydroxy-2-methyl-4-[3-(2-oxo-1,2,3,4 -tetrahydroquinolin-6-ylthio)phenyl]tetrahydropyran in 25% yield, m.p. 180°–181° C. (recrystallised from ethyl acetate);

NMR Spectrum: 1.21 (d, 3H), 1.55–1.8 (m, 4H), 2.1 (m, 1H), 2.64 (m, 2H), 2.90 (m, 2H), 3.85–4.05 (m, 3H), 6.72 (d, 1H), 7.1 (m, 1H), 7.2–7.4 (m, 4H), 7.45 (m, 1H), 7.9 (broad s, 1H).

The 6-mercapto-1,2,3,4-tetrahydroquinolin-2-one used as a starting material was obtained as follows:

Using analogous procedures to those described in the third, fourth and fifth paragraphs of the portion of Example 8 which is concerned with the preparation of starting materials, 1,2,3,4-tetrahydroquinolin-2-one was converted in turn into:

2-oxo-1,2,3,4-tetrahydroquinolin-6-ylsulphonyl chloride in 82% yield, m.p. 205°–208° C.;
di-(2-oxo-1,2,3,4-tetrahydroquinolin-6-yl) disulphide in 95% yield, m.p. 264°–265° C.; and
6-mercapto-1,2,3,4-tetrahydroquinolin-2-one in 70% yield, m.p. 154°–156° C.

EXAMPLE 11

Using an analogous procedure to that described in Example 2, (2S,4R)-4-hydroxy-2-methyl-4-[3-(2-oxo-1,2,3,4-tetrahydroquinolin-6-ylthio)phenyl] tetrahydropyran was oxidised to give (2S,4R)-4-hydroxy-2-methyl-4-[3-(2-oxo-1,2,3,4 -tetrahydroquinolin-6-ylsulphonyl)phenyl]tetrahydropyran in 51% yield, m.p. 178–180° C. (recrystallised from ethyl acetate);

NMR Spectrum: 1.2 (d, 3H), 1.55–1.8 (m, 3H), 1.9 (s, 1H), 2.1 (m, 1H), 2.65 (m, 2H), 3.0 (m, 2H), 3.85–4.05 (m, 3H), 6.85 (d, 1H), 7.5 (t, 1H), 7.68 (m, 1H), 7.7–7.9 (m, 3H), 8.1 (m, 1H), 8.4 (broad s, 1H).

EXAMPLE 12

Using an analogous procedure to that described in Example 2, (2S,4R)-4-[3-(1-ethyl-2-oxo-1,2,3,4-tetrahydroquinolin-6-ylthio)phenyl]-4-hydroxy-2-methyltetrahydropyran was oxidised to give (2S,4R)-4-[3-(1-ethyl-2-oxo-1,2,3,4-tetrahydroquinolin-6-ylsulphonyl)phenyl]-4-hydroxy-2-methyltetrahydropyran in 97% yield, m.p. 122°–124° C. (recrystallised from diethyl ether);

NMR Spectrum: 1.15–1.3 (m, 6H), 1.55–1.8 (m, 4H), 2.1 (m, 1H), 2.65 (m, 2H), 2.95 (m, 2H), 3.85–4.05 (m, 5H), 7.1 (d, 1H), 7.5 (t, 1H), 7.6–7.75 (m, 2H), 7.9 (m, 2H), 8.12 (m, 1H).

EXAMPLE 13

Using an analogous procedure to that described in Example 6, 7-fluoro-6-mercapto-1-methyl-1,2,3,4-tetrahydroquinolin-2-one was reacted with (2S,4R)-4-hydroxy-4-(3-iodophenyl)-2-methyltetrahydropyran to give (2S,4R)-4-[3-(7-fluoro-1-methyl-2-oxo-1,2,3,4 -tetrahydroquinolin-6-ylthio)phenyl]-4-hydroxy-2-methyltetrahydropyran in 55% yield, m.p. 90–92° C. (recrystallised from diethyl ether);

NMR Spectrum: 1.2 (d, 3H), 1.55–1.8 (m, 4H), 2.1 (m, 1H), 2.65 (m, 2H), 2.85 (m, 2H), 3.35 (s, 3H), 3.85–4.05 (m, 3H), 6.78 (d, 1H), 7.1 (m, 1H), 7.2–7.35 (m, 3H), 7.45 (m, 1H).

The 7-fluoro-6-mercapto-1-methyl-1,2,3,4-tetrahydroquinolin-2-one used as a starting material was obtained as follows:

A mixture of 2,4-difluorobenzaldehyde (2.84 g), trimethyl phosphonoacetate (4.5 g), potassium carbonate (3.1 g) and water (2 ml) was stirred vigorously at room temperature for 18 hours. Water (50 ml) was added and the precipitate was isolated and dried. There was thus obtained methyl 2,4-difluorocinnamate (3.2 g, 80%), m.p. 38°–40° C.

A mixture of a portion (3 g) of the material so obtained and a solution of methylamine (16.5 g) in ethanol (50 ml) was stirred at ambient temperature for 3 hours. The mixture was evaporated and the residue was purified by column chromatography using increasingly polar mixtures of hexane and ethyl acetate as eluent. There was thus obtained 2,4-difluoro-N-methylcinnamamide (1.57 g, 45%), m.p. 142°–143° C.

A mixture of the material so obtained, 10% palladium-on-carbon catalyst (0.2 g) and ethanol (50 ml) was stirred under an atmosphere of hydrogen for 2 hours. The mixture was filtered and the filtrate was evaporated to give 3-(2,4-difluorophenyl)-methylpropionamide (1.46 g, 93%), m.p. 90°–91° C.

Sodium hydride (60% dispersion in mineral oil, 0.3 g) was added portionwise to a stirred solution of a portion (1.3 g) of the N-methylpropionamide in NMP (10 ml) and the mixture was stirred at ambient temperature for 3 hours and at 60° C. for 30 minutes. The mixture was cooled to ambient temperature and partitioned between ethyl acetate and water. The organic phase was dried (Na$_2$SO$_4$) and evaporated. The residue was purified by column chromatography using increasingly polar mixtures of hexane and ethyl acetate as eluent. There was thus obtained 7-fluoro-1-methyl-1,2,3,4-tetrahydroquinolin-2-one (0.38 g, 32%) as a gum.

Using analogous procedures to those described in the third, fourth and fifth paragraphs of the portion of Example 8 which is concerned with the preparation of starting materials, 7-fluoro-1-methyl-1,2,3,4-tetrahydroquinolin-2-one was converted in turn into:

7-fluoro-1-methyl-2-oxo-1,2,3,4-tetrahydroquinolin-6-ylsulphonyl chloride in 96% yield, m.p. 122°–124° C.;
di-(7-fluoro-1-methyl-2-oxo-1,2,3,4-tetrahydroquinolin-6-yl) disulphide in 95% yield, m.p. 163°–165° C.; and
7-fluoro-6-mercapto-1-methyl-1,2,3,4-tetrahydroquinolin-2-one in 83% yield, m.p. 114°–115° C.

EXAMPLE 14

Using an analogous procedure to that described in Example 2, (2S,4R)-4-[3-(7-fluoro-1-methyl-2-oxo-1,2,3,4-tetrahydroquinolin-6-ylthio)phenyl]-4-hydroxy-2-methyltetrahydropyran was oxidised to give (2S,4R)-4-[3-(7-fluoro-1-methyl-2-oxo-1,2,3,4-tetrahydroquinolin-6-ylsulphonyl)phenyl]-4-hydroxy-2-methyltetrahydropyran in 64% yield, m.p. 135°–138° C. (recrystallised #from diethyl ether);

NMR Spectrum: 1.2 (d, 3H), 1.55–1.8 (m, 4H), 2.1 (m, 1H), 2.65 (m, 2H), 2.95 (m, 2H), 3.32 (s, 3H), 3.85–4.05 (m, 3H), 6.7 (d, 1H), 7.52 (t, 1H), 7.75 (m, 1H), 7.8–8.0 (m, 2H), 8.15 (m, 1H).

EXAMPLE 15

Using an analogous procedure to that described in Example 6, 5-fluoro-6-mercapto-1-methyl-1,2,3,4-tetrahydroquinolin-2-one was reacted with (2S,4R)-4-hydroxy-4-(3-iodophenyl)-2-methyltetrahydropyran to give (2S,4R)-4-[3-(5-fluoro-1-methyl-2-oxo-1,2,3,4 -tetrahydroquinolin-6-ylthio)phenyl-4-hydroxy-2-methyltetrahydropyran in 82% yield, m.p. 141–142° C. (recrystallised from a mixture of hexane and ethyl acetate);

NMR Spectrum: 1.2 (d, 3H), 1.55–1.8 (m, 4H), 2.1 (m, 1H), 2.65 (m, 2H), 2.95 (m, 2H), 3.35 (s, 3H), 3.85–4.05 (m, 3H), 6.78 (d, 1H), 7.1 (m, 1H).

The 5-fluoro-6-mercapto-1-methyl-1,2,3,4-tetrahydroquinolin-2-one used as a starting material was obtained as follows:

A mixture of 2,6-difluorobenzaldehyde (2.84 g), trimethyl phosphonoacetate (4.5 g), potassium bicarbonate (4 g) and water (2 ml) was stirred vigorously and heated to 100° C. for 1 hour. The mixture was cooled to ambient temperature. Water (50 ml) and hexane (5 ml) were added and the mixture was stirred causing the insoluble gum so deposited to crystallise. There was thus obtained methyl 2,6-difluorocinnamate (3.2 g, 81%), m.p. 48°–50° C.

Using analogous procedures to those described in the second to fifth paragraphs of the portion of Example 13 which is concerned with the preparation of starting materials, methyl 2,6-difluorocinnamate was converted in turn into:

2,6-difluoro-N-methylcinnamamide in 67% yield, m.p. 143°–145° C.;

3-(2,6-difluorophenyl)-N-methylpropionamide in 95% yield, m.p. 115°–117° C.;

5-fluoro-1-methyl-1,2,3,4-tetrahydroquinolin-2-one in 74% yield, m.p. 55°–57° C.;

5-fluoro-1-methyl-2-oxo-1,2,3,4-tetrahydroquinolin-6-ylsulphonyl chloride in 79% yield, m.p. 129°–130° C.;

di-(5-fluoro-1-methyl-2-oxo-1,2,3,4-tetrahydroquinolin-6-yl) disulphide in 91% yield, m.p. 173°–175° C.; and 5-fluoro-6-mercapto-1-methyl-1,2,3,4-tetrahydroquinolin-2-one in 97% yield, m.p. 120–123° C.

EXAMPLE 16

Using an analogous procedure to that described in Example 2, (2S,4R)-4-[3-(5-fluoro-1-methyl-2-oxo-1,2,3,4-tetrahydroquinolin-6ylthio)phenyl]-4-hydroxy-2-methyltetrahydropyran was oxidised to give (2S,4R)-4-[3-(5-fluoro-1-methyl-2-oxo-1,2,3,4-tetrahydroquinolin-6ylsulphonyl)phenyl]-4-hydroxy-2-methyltetrahydropyran in 63% yield, m.p. 149°–151° C. (recrystallised from a mixture of diethyl ether and ethyl acetate);

NMR Spectrum: 1.2 (d, 3H), 1.55–1.9 (m, 4H), 2.1 (m, 1H), 2.65 (m, 2H), 2.9 (m, 2H), 3.35 (s, 3H), 3.85–4.05 (m, 3H), 6.9 (d, 1H), 7.55 (t, 1H), 7.75 (m, 1H), 7.9–8.05 (m, 2H), 8.15 (m, 1H).

EXAMPLE 17

Using an analogous procedure to that described in Example 6, 8-chloro-6-mercapto-1,2,3,4-tetrahydroquinolin-2-one was reacted with (2S,4R)-4-hydroxy-4-(3-iodophenyl)-2-methyltetrahydropyran to give (2S,4R)-4-[3-(8-chloro-2-oxo-1,2,3,4-tetrahydroquinolin-6-ylthio)phenyl]-4-hydroxy-2-methyltetrahydropyran in 69% yield as a gum;

NMR Spectrum: 1.21 (d, 3H), 1.55–1.8 (m, 4H), 2.1 (m, 1H), 2.64 (m, 2H), 2.96 (m, 2H), 3.85–4.05 (m, 3H), 7.1–7.2 (m, 2H), 7.25–7.45 (m, 3H), 7.5 (m, 1H), 7.8 (broad s, 1H).

The 8-chloro-6-mercapto-1,2,3,4-tetrahydroquinolin-2-one used as a starting material was obtained as follows:

A solution of 3-chloropropionyl chloride (19.1 ml) in methylene chloride (80 ml) was added dropwise during 45 minutes to a stirred solution of 2-chloroaniline (43 ml) in methylene chloride (20 ml) which had been cooled to 0° C. The mixture was stirred at 0° C. for 2 hours. Methylene chloride (100 ml) was added and the mixture was washed with water, dried ($Na_2SO_4$) and evaporated. The residue was triturated under hexane. There was thus obtained 3,2'-dichloropropionanilide (39.1 g, 90%), m.p. 79°–80° C.

The material so obtained was added portionwise to aluminium chloride (71.4 g) and the mixture was stirred and heated to 120° C. When the addition was complete, the mixture was heated to 120° C. for 4 hours. The mixture was cooled to 80° C. and poured onto crushed ice. The resultant mixture was extracted with methylene chloride. The organic solution was washed with a saturated aqueous sodium bicarbonate solution, dried ($Na_2SO_4$) and evaporated. There was thus obtained 8-chloro-1,2,3,4-tetrahydroquinolin-2-one (28.1 g, 86%), m.p. 107°–109° C.

Using analogous procedures to those described in the third, fourth and fifth paragraphs of the portion of Example 8 which is concerned with the preparation of starting materials, 8-chloro-1,2,3,4 -tetrahydroquinolin-2-one was converted in turn into:

8-chloro-2-oxo-1,2,3,4-tetrahydroquinolin-6-ylsulphonyl chloride in 84% yield, m.p. 185°–189° C.;

di-(8-chloro-2-oxo-1,2,3,4-tetrahydroquinolin-6-yl) disulphide in 100% yield, m.p. 156°–160° C.; and 8-chloro-6-mercapto-1,2,3,4-tetrahydroquinolin-2-one in 74% yield, m.p. 163°–165° C. (recrystallised from a mixture of hexane and diethyl ether).

EXAMPLE 18

Sodium hydride (50% dispersion in mineral oil, 0.05 g) was added portionwise to a stirred mixture of (2S,4R)-4 -(tert-butyldimethylsilyloxy)-4-[3-(8-chloro-2-oxo-1,2,3,4-tetrahydroquinolin-6-ylthio)phenyl]-2-methyltetrahydropyran (0.25 g), methyl iodide (0.105 g) and DMF (3 ml). The mixture was stirred at ambient temperature for 30 minutes. The mixture was partitioned between a dilute aqueous ammonium chloride solution and diethyl ether. The organic phase was washed with brine, dried ($Na_2SO_4$) and evaporated. A mixture of the residue so obtained and tetrabutylammonium fluoride (0.2M in THF, 5 ml) was stirred and heated to 70° C. for 2 hours. The mixture was evaporated and the residue was purified by column chromatography using increasingly polar mixtures of hexane and ethyl acetate as eluent. There was thus obtained (2S,4R)-4-[3-(8-chloro-1-methyl-2-oxo-1,2,3,4-tetrahydroquinolin-6-ylthio)phenyl]-4-hydroxy-2-methyltetrahydropyran (0.18 g, 89%) as a gum;

NMR Spectrum: 1.21 (d, 3H), 1.55–1.8 (m, 4H), 2.1 (m, 1H), 2.58 (m, 2H), 2.8 (m, 2H), 3.45 (s, 3H), 3.85–4.05 (m, 3H), 7.04 (m, 1H), 7.2–7.45 (m, 4H), 7.55 (m, 1H).

The (2S,4R)-4-(tert-butyldimethylsilyloxy)-4-[3-(8-chloro-2-oxo-1,2,3,4-tetrahydroquinolin-6-ylthio)phenyl]-2-methyltetrahydropyran used as a starting material was obtained as follows:

Sodium hydride (50% dispersion in mineral oil, 0.3 g) was added portionwise to a stirred mixture of (2S,4R)-4-hydroxy-4-(3-iodophenyl)-2-methyltetrahydropyran (1.64 g), 1,4,7,10,13-pentaoxacyclopentadecane (hereinafter 15-crown-5, 0.05 g) and THF (30 ml) and the mixture was stirred at ambient temperature for 30 minutes. Tert-butyldimethylsilyl chloride (0.9 g) was added and the mixture was stirred and heated to 60° C. for 6 hours. The mixture was cooled to ambient temperature and partitioned between diethyl ether and a dilute aqueous ammonium chloride solution. The organic solution was washed with brine, dried ($Na_2SO_4$) and evaporated. The residue was purified by column chromatography using increasingly polar mixtures of hexane and ethyl acetate as eluent. There was thus obtained (2S,4R)-4-(tert-butyldimethylsilyloxy)-4-(3-iodophenyl)-2-methyltetrahydropyran (1.9 g, 88%) as an oil.

The material so obtained was reacted with 8-chloro-6-mercapto-1,2,3,4-tetrahydroquinolin-2-one using an analogous procedure to that described in Example 6. There was thus obtained (2S,4R)-4-(tert-butyldimethylsilyloxy)-4-[3-(8-chloro-2-oxo-1,2,3,4-tetrahydroquinolin-6-ylthio)phenyl]-2-methyltetrahydropyran in 77% yield as a gum.

EXAMPLE 19

Using an analogous procedure to that described in Example 18, (2S,4R)-4-(tert-butyldimethylsilyloxy)-2-methyl-4-[3-(2-oxo-1,2,3,4-tetrahydroquinolin-6-ylthio)phenyl]tetrahydropyran was reacted with allyl chloride and the resultant product was treated with tetrabutylammonium fluoride to give (2S,4R)-4-[3-(1-allyl-2-oxo-1,2,3,4-tetrahydroquinolin-6-ylthio)phenyl]-4-hydroxy-2-methyltetrahydropyran in 86% yield, m.p. 107°–109° C. (recrystallised from diethyl ether);

NMR Spectrum: 1.2 (d, 3H), 1.55–1.8 (m, 4H), 2.1 (m, 1H), 2.7 (m, 2H), 2.9 (m, 2H), 3.85–4.05 (m, 3H), 4.55 (m, 2H), 5.1–5.3 (m, 2H), 5.75–6.0 (m, 1H), 6.95 (d, 1H), 7.12 (d, 1H), 7.2–7.4 (m, 4H), 7.5 (m, 1H).

The (2S,4R)-4-(tert-butyldimethylsilyloxy)-2-methyl-4-[3-(2-oxo-1,2,3,4-tetrahydroquinolin-6-ylthio)phenyl]tetrahydropyran used as a starting material was obtained by the reaction of 6-mercapto-1,2,3,4-tetrahydroquinolin-2-one with (2S,4R)-4-(tert-butyldimethylsilyloxy)-4-(3-iodophenyl)-2-methyltetrahydropyran using an analogous procedure to that described in Example 6. There was thus obtained the required starting material in 36% yield as a gum.

EXAMPLE 20

The procedure described in Example 19 was repeated except that 3-trimethylsilylprop-2-ynyl bromide was used in place of allyl chloride. There was thus obtained (2S,4R)-4-hydroxy-2-methyl-4-{3-[2-oxo-1-(2-propynyl)-1,2,3,4-tetrahydroquinolin-6-ylthio]phenyl}-tetrahydropyran in 22% yield, m.p. 110°–113° C. (recrystallised from diethyl ether);

NMR Spectrum: 1.21 (d, 3H), 1.55–1.8 (m, 4H), 2.1 (m, 1H), 2.24 (m, 1H), 2.7 (m, 2H), 2.88 (m, 2H), 3.85–4.05 (m, 3H), 4.7 (d, 1H), 7.1–7.4 (m, 6H), 7.5 (m, 1H).

EXAMPLE 21

A mixture of (2S,4R)-4-hydroxy-2-methyl-4-[3-(1-methyl-2-oxo-1,2,3,4-tetrahydroquinolin-6-ylthio)phenyl]tetrahydropyran (0.15 g), potassium peroxymonosulphate (0.12 g), water (1 ml) and ethanol (2 ml) was stirred vigorously at ambient temperature for 30 minutes. Water (10 ml) was added and the mixture was extracted with ethyl acetate. The organic solution was dried ($Na_2SO_4$) and evaporated. The residue was purified by column chromatography using increasingly polar mixtures of hexane and ethyl acetate as eluent. There was thus obtained (2S,4R)-4-hydroxy-2-methyl-4-[3-(1-methyl-2-oxo-1,2,3,4-tetrahydroquinolin-6-ylsulphinyl)phenyl]tetrahydropyran (0.06 g, 38%) as a gum;

NMR Spectrum: ($CD_3SOCD_3$ +$CD_3CO_2D$) 1.1 (d, 3H), 1.45–1.7 (m, 4H), 2.5 (m, 2H), 2.9 (m, 2H), 3.22 (s, 3H), 3.7–4.0 (m, 3H), 7.18 (m, 1H), 7.4–7.65 (m, 5H), 7.88 (m, 1H).

EXAMPLE 22

A mixture of (2S,4R)-4-hydroxy-2-methyl-4-[3-(1-methyl-2-oxo-1,2,3,4-tetrahydroquinolin-6-ylthio)phenyl]tetrahydropyran (0.1 g), acetic anhydride (1 ml) and glacial acetic acid (1 ml) was stirred and heated to reflux for 4 hours. The mixture was cooled to ambient temperature and partitioned between ethyl acetate and water. The organic phase was dried ($Na_2SO_4$) and evaporated. The residue was purified by column chromatography using increasingly polar mixtures of hexane and ethyl acetate as eluent. There was thus obtained (2S,4R)-4-acetoxy-2-methyl-4-[3-(1-methyl-2-oxo-1,2,3,4-tetrahydroquinolin-6-ylthio)phenyl]tetrahydropyran (0.05 g, 45%) as a gum;

NMR Spectrum: 1.21 (d, 3H), 1.65 (m, 1H), 1.9–2.1 (m, 4H), 2.4 (m, 2H), 2.65 (m, 2H), 2.87 (m, 2H), 3.35 (s, 3H), 3.7–4.05 (m, 3H), 6.93 (d, H), 7.1–7.4 (m, 6H).

EXAMPLE 23

A mixture of (2S,4R)-4-hydroxy-2-methyl-4-[3-(1-methyl-2-oxo-1,2,3,4-tetrahydroquinolin-6-ylthio)phenyl]tetrahydropyran (0.05 g), sodium thiomethoxide (0.05 g) and NMP (0.5 ml) was stirred and heated to 120° C. for 18 hours. A second portion of sodium thiomethoxide (0.05 g) was added and the mixture was stirred at 120° C. for a further 24 hours. The mixture was cooled to ambient temperature and partitioned between ethyl acetate and water. The organic phase was dried ($Na_2SO_4$) and evaporated. The residue was purified by column chromatography using increasingly polar mixtures of hexane and ethyl acetate as eluent. There was thus obtained (2S,4R)-4-hydroxy-2-methyl-4-[3-(1-methyl-2-oxo-1,2-dihydroquinolin-6-ylthio)phenyl]tetrahydropyran (0.02 g, 40%), m.p. 134°–137° C. (recrystallised from diethyl ether);

NMR Spectrum: 1.2 (d, 3H), 1.55–1.8 (m, 4H), 2.1 (m, 1H), 3.72 (s, 3H), 3.85–4.05 (m, 3H), 6.72 (d, 1H), 7.12 (m, 1H), 7.25–7.4 (m, 3H), 7.5 (m, 1H), 7.56–7.64 (m, 3H).

EXAMPLE 24

Using an analogous procedure to that described in Example 6, 5-mercapto-1-methylindolin-2-one was reacted with (2S,4R)-4-hydroxy-4-(3-iodophenyl)-2-methyltetrahydropyran to give (2S,4R)-4-hydroxy-2-methyl-4-[3-(1-methyl-2-oxoindolin-5-ylthio)phenyl]tetrahydropyran in 55% yield, m.p. 110°–111° C. (recrystallised from a mixture of diethyl ether and ethyl acetate);

NMR Spectrum: 1.2 (d, 3H), 1.55–1.8 (m, 4H), 2.1 (m, 1H), 3.22 (s, 3H), 3.50 (m, 2H), 3.85–4.05 (m, 3H), 6.8 (d, 1H), 7.05 (m, 1H), 7.2–7.35 (m, 3H), 7.4–7.5 (m, 2H).

The 5-mercapto-1-methylindolin-2-one used as a starting material was obtained as follows:

A solution of potassium hydroxide (46 g) in a mixture of water (5 ml) and methanol (55 ml) was added to a stirred mixture of 2-oxoindoline (21.8 g) and methanol (40 ml) which had been cooled in an ice-bath. The mixture was stirred for 20 minutes. Dimethyl sulphate (77 ml) was added dropwise to the mixture which was stirred and cooled in an ice-bath. The mixture was allowed to warm to ambient temperature and was stirred for 3 hours. The mixture was filtered and the filtrate was evaporated. The residue was partitioned between ethyl acetate and water. The organic phase was dried (MgSO$_4$) and evaporated. The residue was purified by column chromatography using a 7:3 mixture of petroleum ether (b.p. 40°–60° C.) and ethyl acetate as eluent. There was thus obtained 1-methyl-2-oxoindoline (18 g, 75%), m.p. 83°–85° C.

A portion (1 g) of the material so obtained was added portionwise to chlorosulphonic acid (6.2 ml) which was stirred and cooled to 0° C. The mixture was stirred at 0° C. for 30 minutes and then heated to 60° C. for 2 hours. The mixture was cooled to ambient temperature, poured onto a mixture of ice and water and extracted with diethyl ether. The organic solution was washed with brine, dried (MgSO$_4$) and evaporated. The residue was purified by column chromatography using a 33:17 mixture of petroleum ether (b.p. 40–60° C.) and ethyl acetate as eluent. There was thus obtained 1-methyl-2-oxoindolin-5 -ylsulphonyl chloride (1.6 g, 87%), m.p. 159° C.

A portion (0.95 g) of the material so obtained was added to aqueous hydroiodic acid (57%, 2.7 ml) and the mixture was stirred and heated to 100° C. for 90 minutes. The mixture was cooled to ambient temperature and sodium metabisulphite was added portionwise to remove the brown colouration resulting from the presence of iodine. The mixture was partitioned between ethyl acetate and a saturated aqueous sodium metabisulphite solution. A precipitate was deposited which was isolated and dried. There was thus obtained di-(1-methyl-2-oxoindolin-5-yl) disulphide (0.6 g, 44%), m.p. 155° C.

Triphenylphosphine (0.865 g) was added to a mixture of di-(1-methyl-2-oxoindolin-5-yl) disulphide (1 g), water (1.25 ml) and 1,4-dioxan (15 ml) and the mixture was stirred and heated to 100° C. for 16 hours. The bulk of the organic solvent was evaporated and the mixture was basified to pH 12 by the addition of 2N aqueous sodium hydroxide solution. The basic solution was washed with methylene chloride and acidified by the addition of 2N aqueous hydrochloric acid. The aqueous mixture was extracted with methylene chloride. The resultant organic solution was washed with brine, dried (MgSO$_4$) and evaporated. There was thus obtained 5-mercapto-1-methylindolin-2-one (0.83 g, 82%), m.p. 100°–101° C.

EXAMPLE 25

Using an analogous procedure to that described in Example 5, 7-fluoro-6-iodo-1-methyl-1,2,3,4-tetrahydroquinolin-2-one was reacted with (2S,4R)-4-hydroxy-4-(2-mercaptothien-4-yl)-2-methyltetrahydropyran to give 4-[2-(7-fluoro-1-methyl-2-oxo-1,2,3,4-tetrahydroquinolin-6 -ylthio)thien-4-yl]-4-hydroxy-2-methyltetrahydropyran in 85% yield as a gum;

NHR Spectrum: 1.2 (d, 3H), 1.55–1.85 (m, 4H), 2.1 (m, 1H), 2.65 (m, 2H), 2.8 (m, 2H), 3.3 (s, 3H), 3.85–4.05 (m, 3H), 6.7 (d, 1H), 7.07 (d, 1H), 7.25 (m, 2H).

The 7-fluoro-6-iodo-1-methyl-1,2,3,4-tetrahydroquinolin-2-one used as a starting material was obtained as follows:

A mixture of 7-fluoro-1-methyl-1,2,3,4-tetrahydroquinolin-2-one (0.4 g), iodine monochloride (0.6 g) and glacial acetic acid (3 ml) was stirred and heated to 80° C. for 1 hour. The mixture was cooled to ambient temperature, poured into a dilute aqueous sodium metabisulphite solution and extracted with ethyl acetate. The organic solution was dried (Na$_2$SO$_4$) and evaporated. The residue was purified by column chromatography using increasingly polar mixtures of hexane and ethyl acetate as eluent. There was thus obtained 7-fluoro-6-iodo-1-methyl-1,2,3,4-tetrahydroquinolin-2-one (0.45 g, 66%), m.p. 125–126° C. (recrystallised from a mixture of hexane and diethyl ether).

EXAMPLE 26

A mixture of 7-fluoro-6-mercapto-1-methyl-1,2,3,4 -tetrahydroquinolin-2-one (0.25 g), (2S,4R)-4-(2-chlorothiazol-5-yl)-4-hydroxy-2 -methyltetrahydropyran (0.22 g), potassium carbonate (0.2 g) and DHF (2 ml) was stirred and heated to 100° C. for 2 hours. The mixture was cooled to ambient temperature and partitioned between ethyl acetate and water. The organic solution was dried (Na$_2$S04) and evaporated. The residue was purified by column chromatography using increasingly polar mixtures of hexane and ethyl acetate as eluent. There was thus obtained (2S,4R)-4-[2-(7-fluoro-1-methyl-2-oxo-1,2,3,4 -tetrahydroquinolin-6-ylthio)thiazol-5-yl]-4-hydroxy-2-methyltetrahydropyran (0.25 g, 61%) as a gum;

NMR Spectrum: 1.2 (d, 3H), 1.55–2.[(m, 4H), 2.2 (s, 1H), 2.65 (m, 2H), 2.9 (m, 2H), 3.35 (s, 3H), 3.8–4.0 (m, 3H), 6.85 (d, 1H), 7.42 (d, 1H), 7.45 (s, 1H).

EXAMPLE 27

Using an analogous procedure to that described in Example 26 except that NMP was used in place of DMF as reaction solvent, 5-mercapto-1-methylindolin-2-one was reacted with (2S,4R)-4-(2 -chlorothiazol-5-yl)-4-hydroxy-2-methyltetrahydropyran to give (2S,4R)-4-hydroxy-2-methyl-4-[2-(1-methyl-2-oxoindolin-5 -ylthio)thiazol-5-yl]tetrahydropyran in 27% yield, m.p. 140° C.;

NMR Spectrum: 1.17–1.19 (d, 3H), 1.63–1.69 (m, 1H), 1.73–1.78 (m, 1H), 1.82–1.87 (m, 1H), 1.91 (s, 1H), 1.98–2.04 (m, 1H), 3.24 (s, 3H), 3.56 (s, 2H), 3.84–3.89 (m, 3H), 6.86–6.88 (d, 1H), 7.46 (s, 1H), 7.52–7.53 (m, 1H), 7.61–7.63 (m, 1H).

EXAMPLE 28

Potassium tert-butoxide (1.66 g) was added portionwise to a stirred solution of (2S,4R)-4-hydroxy-4-(2-mercaptothien-4-yl)-2methyltetrahydropyran (3.15 g) in DMSO (25 ml) and the mixture was stirred at ambient temperature for 5 minutes. 5-Bromo-1-methylindolin2-one (3.71 g) and tetrakis(triphenylphosphine)palladium(O) (1.59 g) were added and the mixture was heated to 100° C. for 75 minutes. The mixture was cooled to ambient temperature and partitioned between ethyl acetate and a mixture of ice and water. The organic phase was washed with brine, dried (MgSO$_4$) and evaporated. The residue was purified by column chromatography using increasingly polar mixtures of petroleum ether (b.p. 40°–60° C.) and ethyl acetate as eluent. The material so obtained was further purified by column chromatography using a 5:1 mixture of methylene chloride and acetone as eluent. There was thus obtained (2S,4R)-4-hydroxy-2-methyl-4-[2-(1-methyl-2-oxoindolin-5 -ylthio-)thien-4-yl]tetrahydropyran (2.45 g, 48%), m.p. 125°–127° C. (recrystallised from diethyl ether containing a few drops of methylene chloride) and m.p. 129.5°–130.5° C. after a further recrystallisation from ethyl acetate;

NMR Spectrum: 1.15 (d, 3H), 1.70 (m, 4H), 1.95 (m, 1H), 3.12 (s, 3H), 3.40 (s, 2H), 3.85 (m, 3H), 6.68 (d, 1H), 7.18 (m, 3H), 7.27 (d, 1H).

The 5-bromo-1-methylindolin-2-one used as a starting material was obtained as follows:

Bromine (3.36 ml) was added to a solution of potassium bromide (15.55 g) in water (57 ml). The resultant mixture was added dropwise to a stirred solution of 1-methyl-2-oxoindoline (9.58 g) in water (285 ml) which had been heated to 80° C. When the addition was complete the mixture was cooled to ambient temperature and the precipitate was isolated. The material so obtained was dissolved in ethyl acetate. The organic solution was washed with water and with brine, dried (MgSO$_4$) and evaporated. The residue was purified by column chromatography using a 1:1 mixture of petroleum ether (b.p. 40°–60° C.) and diethyl ether as eluent. There was thus obtained 5-bromo-1-methylindolin-2-one (11.3 g, 77%), m.p. 134°–135° C.

EXAMPLE 29 n-Butyl-lithium (1.6M in hexane, 1.4 ml) was added dropwise to a solution of (2S,4R)-4-(tert-butyldimethylsilyloxy)-2-methyl-4(2-thienyl)tetrahydropyran (0.624 g) in THF (20 ml) which had been cooled to –50° C. The reaction mixture was stirred at –25° C. for 90 minutes. The mixture was recooled to –70° C. and a solution of di-(1-methyl-2-oxo-1,2,3,4-tetrahydroquinolin-6-yl) disulphide (0.8 g) in THF (20 ml) was added. The mixture was stirred at –70° C. for 1 hour and then allowed to warm to 0° C. The mixture was partitioned between diethyl ether and a saturated aqueous ammonium chloride solution. The organic phase was washed with brine, dried (MgSO$_4$) and evaporated. The residue was purified by column chromatography using a 5:1 mixture of hexane and ethyl acetate as eluent. A solution of the residue (0.55 g) so obtained in THF (20 ml) was cooled to 0° C. and tetrabutylammonium fluoride (1M in THF, 1.6 ml) was added. The mixture was allowed to warm to ambient temperature and was stirred for 2 hours. The mixture was partitioned between diethyl ether and a saturated aqueous sodium bicarbonate solution. The organic phase was washed with brine, dried (MgSO$_4$) and evaporated. The residue was purified by column chromatography using a 3:7 mixture of hexane and ethyl acetate as eluent. There was thus obtained (2S,4R)-4-hydroxy-2-methyl-4-[2-(1 -methyl-2-oxo-1,2,3,4-tetrahydroquinolin-6-ylthio)thien-5-yl]-tetrahydropryan (0.393 g, 48%), m.p. 50°–52° C.

The (2S,4R)-4-(tert-butyldimethylsilyloxy)-2-methyl-4-(2thienyl)tetrahydropyran used as a starting material was obtained as follows:

A solution of (2S)-2-methyltetrahydropyran-4-one (0.627 g) in toluene (1 ml) was added to the Grignard reagent prepared from 2-bromothiophene (0.82 g) and magnesium turnings (0.15 g) in diethyl ether (7 ml). The mixture was stirred at ambient temperature for 90 minutes. The mixture was partitioned between diethyl ether and a saturated aqueous ammonium chloride solution. The organic solution was washed with brine, dried (MgSO$_4$) and evaporated. The residue was purified by column chromatography using a 5:1 mixture of hexane and ethyl acetate as eluent. There were thus obtained: (2S,4R)-4-hydroxy-2-methyl-4-(2-thienyl)tetrahydropyran (0.48 g, 48%) and the corresponding (2S,4S)-isomer (0.35 g, 35%).

After repetition of the preceding step, a solution of the (2S,4R)-isomer (0.81 g) in THF (22 ml) was added to a stirred mixture of potassium hydride (35% dispersion in mineral oil, 0.56 g), 1,4,7,10,13,16-hexaoxacyclooctadecane (hereinafter 18-crown-6, 0.012 g) and THF (4 ml) which had been cooled in an ice-bath. The mixture was stirred at 0° C. for 10 minutes. A solution of tert-butyldimethylsilyl chloride (0.685 g) in THF (4 ml) was added and the mixture was stirred at ambient temperature for 16 hours. The mixture was partitioned between diethyl ether and a saturated aqueous sodium bicarbonate solution. The organic solution was washed with brine, dried (MgSO$_4$) and evaporated. The residue was purified by column chromatography using a 10:1 mixture of hexane and ethyl acetate as eluent. There was thus obtained (2S,4R)-4-(tert-butyldimethylsilyloxy)-2-methyl-4 -(2-thienyl)tetrahydropyran (0.63 g, 50%) as an oil;

NMR Spectrum: 0.3 (s, 6H), 0.85 (s, 9H), 1.18 (d, 3H), 1.6–1.72 (m, 1H), 1.96–2.13 (m, 3H), 3.61–3.95 (m, 3H), 6.7–6.98 (m, 2H), 7.20 (m, 1H).

EXAMPLE 30

Using an analogous procedure to that described in Example 4, (2S,4R)-4-hydroxy-2-methyl-4-[2-(1-methyl-2-oxo-1,2,3,4 -tetrahydroquinolin-6-ylthio)thien-5-yl]tetrahydropyran was oxidised to give (2S,4R)-4-hydroxy-2-methyl-4-[2-(1-methyl-2-oxo-1,2,3,4-tetrahydroquinolin-6-ylsulphonyl)thien-5-yl]tetrahydropyran in 59% yield, m.p. 80–82° C.

EXAMPLE 31

Using an analogous procedure to that described in Example 5, 6-iodo-1-methyl-1,2,3,4-tetrahydroquinolin-2-one was reacted with 4-hydroxy-4-(2-mercaptothien-4-yl)-2,6-dimethyltetrahydropyran to give 4-hydroxy-2,6-dimethyl-4-[2-(1-methyl-2-oxo-1,2,3,4-tetrahydroquinolin-6-ylthio)thien-4-yl]tetrahydropyran in 62% yield as a foam;

NMR Spectrum: 1.2 (d, 6H), 1.6–1.9 (m, 4H), 2.6 (m, 2H), 2.9 (m, 2H), 3.3 (s, 3H), 4.0 (m, 2H), 6.9–7.3 (m, 5H); with the hydroxy group and each methyl group all being in a cis-relationship.

The 4-hydroxy-4-(2-mercaptothien-4-yl)-2,6-dimethyltetrahydropyran used as a starting material was obtained as follows:

The procedures described in the last two paragraphs of the portion of Example 5 which is concerned with the preparation of starting materials were repeated except that 2,6-dimethyltetrahydro- pyran-4-one was used in place of (2S)-2-methyltetrahydropyran-4-one. There was thus obtained the required starting material as a liquid which was used immediately due to its tendency to be oxidised to the corresponding disulphide.

EXAMPLE 32

Using an analogous procedure to that described in Example 5, 6-iodo-1-methyl-1,2-dihydroquinolin-2-one (European Patent Application No. 0420511, Example 1 thereof) was reacted with (2S,4R)-4-hydroxy-4(2-mercaptothien-4-yl)-2-methyltetrahydropyran to give (2S,4R)-4-hydroxy-2-methyl-4-[2-(1-methyl-2-oxo-1,2 -dihydroquinolin-6-ylthio)thien-4-yl]tetrahydropyran in 65% yield as a foam;

NMR Spectrum: 1.2 (d, 3H), 1.6 (s, 1H), 1.7–1.9 (m, 3H), 2.1 (m, 1H), 3.7 (s, 3H), 4.0 (m, 3H), 6.7 (d, 1H), 7.3 (d, 3H), 7.5 (m, 3H).

EXAMPLE 33

Using an analogous procedure to that described in Example 5, 6-iodo-1,8-dimethyl-1,2,3,4-tetrahydroquinolin-2-one was reacted with (2S,4R)-4-hydroxy-4-(2-mercaptothien-4-yl)-2-methyltetrahydropyran to give (2S,4R)-4-hydroxy-2-methyl-4-[2-(1,8-dimethyl-2-oxo-1,2,3,4-tetrahydroquinolin-6-ylthio)thien-4-yl]tetrahydropyran in 60% yield as a foam;

NMR Spectrum: 1.2 (d, 3H), 1.6 (s, 1H), 1.65–1.9 (m, 4H), 2.1 (m, 1H), 2.3 (s, 3H), 2.5 (q, 2H), 2.8 (q, 2H), 3.3 (s, 3H), 3.9 (m, 3H), 7.0 (d, 2H), 7.3 (d, 2H).

The 6-iodo-1,8-dimethyl-1,2,3,4-tetrahydroquinolin-2-one used as a starting material was obtained as follows:

A mixture of 8-methylquinoline (7 g), methyl iodide (17 ml) and acetonitrile (30 ml) was stirred and heated to 60° C. for 8 days. The mixture was cooled to ambient temperature and diethyl ether (100 ml) was added. The precipitate was isolated and washed with diethyl ether. There was thus obtained 1,8-dimethylquinolinium iodide (12 g).

The material so obtained was added portionwise to a stirred solution of potassium ferricyamide (51 g) in aqueous sodium hydroxide solution (10% weight/volume, 120 ml) which had been cooled to approximately 5° C. The mixture was stirred at ambient temperature for 4 hours. The mixture was partitioned between ethyl acetate and water. The organic solution was washed with water and with brine, dried (MgSO$_4$) and evaporated. There was thus obtained 1,8-dimethyl-1,2-dihydroquinolin-2-one (6g, 79%);

NMR Spectrum: (CD$_3$SOCD$_3$) 2.7 (s, 3H), 3.8 (s, 3H), 6.6 (d, 1H), 7.1 (t, 1H), 7.4 (d, 1H), 7.5 (d, 1H), 7.8 (d, 1H).

A mixture of the material so obtained, 10% palladium-on-carbon catalyst (2 g) and ethanol (200 ml) was stirred under 5 atmospheres pressure of hydrogen for 36 hours. The mixture was filtered and evaporated. There was thus obtained 1,8-dimethyl-1,2,3,4-tetrahydroquinolin-2-one (5.4 g, 88%).

A mixture of a portion (0.28 g) of the material so obtained, iodine monochloride (0.27 g) and glacial acetic acid (3 ml) was stirred and heated to 80° C. for 3 hours. A further portion (0.27 g) of iodine monochloride was added and the mixture was heated to 80° C. for 16 hours. The mixture was cooled to ambient temperature and poured into a saturated aqueous sodium bicarbonate solution. The resultant mixture was extracted with ethyl acetate. The organic solution was washed with water and with brine, dried (MgSO$_4$) and evaporated. There was thus obtained 6-iodo-1,8-dimethyl-1,2,3,4-tetrahydroquinolin-2-one (0.38 g, 79%).

NMR Spectrum: 2.3 (s, 3H), 2.5 (m, 2H), 2.8 (m, 2H), 3.3 (s, 3H), 7.3 (s, 1H), 7.4 (s, 1H).

EXAMPLE 34

Using an analogous procedure to that described in Example 4, (2S,4R)-4-hydroxy-2-methyl-4-[2-(1,8-dimethyl-2-oxo-1,2,3,4-tetrahydroquinolin-6-ylthio)thien-4-yl]tetrahydropyran was oxidised to give (2S,4R)-4-hydroxy-2-methyl-4-[2-(1,8-dimethyl-2-oxo-1,2,3,4-tetrahydroquinolin-6-ylsulphonyl)thien-4-yl]tetrahydropyran in 77% yield;

NMR Spectrum: 1.2 (m, 3H), 1.6–1.9 (m, 4H), 2.0 (m, 1H), 2.4 (s, 3H), 2.6 (q, 2H), 2.9 (q, 2H), 3.4 (s, 3H), 3.9 (m, 3H), 7.5 (d, 1H), 7.6 (s, 1H), 7.7 (d, 2H).

EXAMPLE 35

Using an analogous procedure to that described in Example 5, 8-fluoro-6-iodo-1-methyl-1,2,3,4-tetrahydroquinolin-2-one with (2S,4R)-4-hydroxy-4-(2-mercaptothien-4-yl)-2-methyltetrahydropyran to give (2S,4R)-4-[2-(8-fluoro-1-methyl-2-oxo-1,2,3,4-tetrahydroquinolin-6-ylthio)thien-4-yl]-4-hydroxy-2-methyltetrahydropyran in 40% yield as a foam;

NMR Spectrum: 1.2 (d, 3H), 1.7 (m, 6H), 2.1 (m, 2H), 2.6 (m, 2H), 2.8 (m, 2H), 3.4 (d, 3H), 3.9 (m, 3H), 6.8 (d, 2H), 7.4 (d, 2H).

The 8-fluoro-6-iodo-1-methyl-1,2,3,4-tetrahydroquinolin-2-one used as a starting material was obtained as follows:

Formic acid (3 g) was added dropwise to acetic anhydride (5.4 g) which had been cooled to 0° C. The mixture was stirred at 0° C. for 15 minutes and then heated to 55° C. for 2 hours. The mixture was cooled to ambient temperature. THF (5 ml) and a solution of 2-fluoroaniline (2.22 g) in THF (15 ml) were added and the mixture was stirred at ambient temperature for 2 hours. The mixture was evaporated to give 2'-fluoroformanilide (2.8 g) which was used without further purification.

Borane: dimethyl sulphide complex (5 ml) was added dropwise to a stirred solution of 2'-fluoroformanilide (2.8 g) in THF (12 ml) which had been cooled to 0° C. The mixture was stirred at 0° C. for 15 minutes and then heated to reflux for 2.5 hours. The mixture was recooled to 0° C. and methanol (8 ml) was added dropwise. The mixture was stirred at ambient temperature for 1 hour. The mixture was acidified to pH2 by the introduction of hydrogen chloride gas and the resulting mixture was heated to reflux for 1 hour. The mixture was evaporated and the residue was partitioned between diethyl ether and dilute aqueous sodium hydroxide solution. The organic solution was washed with water and with brine, dried (MgSO$_4$) and evaporated. The residue was purified by column chromatography using hexane as eluent. There was thus obtained 2-fluoro-N-methylaniline (1.59 g, 59%) as a liquid.

After repetition of the preceding steps, 2-fluoro-N-methylaniline (3.8 g) was added dropwise to a stirred solution of 3-chloropropionyl chloride (1.93 g) in methylene chloride (30 ml) which had been cooled to 0° C. The mixture was stirred at 0° C. for 1 hour and stored at 3° C. for 16 hours. The mixture was washed with cold 1N hydrochloric acid solution, with water and with brine, dried (MgSO$_4$) and evaporated. There was thus obtained 3-chloro-2'-fluoromethylpropionanilide (3.74 g, 57%).

The material so obtained was added portionwise to aluminium chloride (7.46 g) and the mixture was stirred and heated to 100° C. for 1 hour. The mixture was cooled to approximately 80° C. and poured onto crushed ice. The resultant mixture was extracted with diethyl ether. The organic solution was washed with water and with brine, dried (MgSO$_4$) and evaporated. The residue was purified by column chromatography using a 10:3 mixture of hexane and ethyl acetate as eluent. There was thus obtained 8-fluoro-1-methyl-1,2,3,4-tetrahydro- quinolin-2-one (1.84 g, NMR Spectrum: 2.6 (m, 2H), 2.9 (m, 2H), 3.5 (d, 3H), 7.0 (m, 3H).

A mixture of the tetrahydroquinolin-2-one so obtained, iodine monochloride (2.15 g) and glacial acetic acid (30 ml) was stirred and heated to 80° C. for 16 hours. A further portion (1.65 g) of iodine monochloride was added and the mixture was heated to 80° C. for 3 hours. The mixture was cooled to ambient temperature and poured slowly into a saturated aqueous sodium bicarbonate solution. The mixture was extracted with ethyl acetate. The organic solution was washed with water and with brine, dried (MgSO$_4$) and evaporated. The residue was purified by column chromatography using a 10:3 mixture of hexane and ethyl acetate as eluent. There was thus obtained 8-fluoro-6-iodo-1-methyl-1,2,3,4-tetrahydroquinolin-2-one (1.1 g, 36%);

NMR Spectrum: 2.6 (m, 2H), 2.9 (m, 2H), 3.4 (s, 3H), 7.2 (m, 2H).

EXAMPLE 36

Using an analogous procedure to that described in Example 5, 6-iodo-1-methyl-1,2,3,4-tetrahydroquinolin-2-one was reacted with 4-hydroxy-4-(2-mercaptothien-4-yl)-2,2-dimethyltetrahydropyran to give 4-hydroxy-2,2-dimethyl-4-[2-(1-methyl-2-oxo-1,2,3,4-tetrahydroquinolin-6-ylthio)thien-4-yl]tetrahydropyran in 72% yield as a foam;

NMR Spectrum: 1.2 (s, 3H), 1.47 (s, 3H), 1.7–1.8 (m, 1H), 1.85 (s, 2H), 2.0–2.2 (m, 1H), 2.6–2.68 (m, 2H), 2.8–2.9 (m, 2H), 3.3 (s, 3H), 3.7–3.8 (m, 1H), 4.02–4.18 (m, 1H), 6.85–7.2 (m, 3H), 7.28 (m, 2H).

The 4-hydroxy-4-(2-mercaptothien-4-yl)-2,2-dimethyltetrahydropyran used as a starting material was obtained as follows:

n-Butyl-lithium (1.4M in hexane, 4.2 ml) was added dropwise to a stirred solution of 4-bromo-2-methylthiothiophene (1.24 g) in diethyl ether (35 ml) which had been cooled to −85° C. The mixture was stirred at −70° C. for 1 hour. A solution of 2,2-dimethyltetrahydropyran- 4-one (European Patent Application No. 0375404, Example 48 thereof; 0.75 g) in diethyl ether (5 ml) was added. The mixture was stirred at −70° C. for i hour and then allowed to warm to −30° C. The mixture was poured into a mixture of ice and a saturated aqueous ammonium chloride solution. The organic solution was washed with brine, dried (MgSO$_4$) and evaporated. The residue was purified by column chromatography using a 10:3 mixture of hexane and ethyl acetate as eluent. There was this obtained 4-hydroxy-2,2-dimethyl-4-(2 -methylthiothien-4-yl)tetrahydropyran (1.0 g, 66%).

NMR Spectrum: 1.2 (s, 3H), 1.46 (s, 3H), 1.57–1.85 (m, 3H), 2.0–2.2 (m, 1H), 2.5 (s, 3H), 3.7–3.8 (m, 1H), 4.0–4.2 (m, 1H), 7.08 (d, 1H), 7.1 (d, 1H).

A mixture of a portion (0.27 g) of the material so obtained, sodium methanethiolate (0.28 g) and DMF (3 ml) was stirred and heated to 130° C. for 40 minutes. The mixture was cooled to ambient temperature and partitioned between ethyl acetate and a dilute aqueous citric acid solution. The organic solution was washed with brine, dried (MgSO$_4$) and evaporated. There was thus obtained 4-hydroxy-4-(2-mercaptothien-4-yl)-2,2-dimethyltetrahydropyran which was used without further purification.

EXAMPLE 37

Using an analogous procedure to that described in Example 4, 4-hydroxy-2,2-dimethyl-4-[2-(1-methyl-2-oxo-1,2,3,4-tetrahydroquinolin-6-ylthio)thien-4-yl]tetrahydropyran was oxidised to give 4-hydroxy-2,2-dimethyl-4-[2-(1-methyl-2-oxo-1,2,3,4 -tetrahydroquinolin-6-ylsulphonyl)thien-4-yl]tetrahydropyran in 95% yield;

NMR Spectrum: 1.2 (s, 3H), 1.45 (s, 3H), 1.65 (m, 1H), 1.8 (s, 2H), 2.02 (m, 1H), 2.65 (m, 2H), 2.95 (m, 2H), 3.75 (m, 1H), 4.05 (m, 1H), 7.07 (d, 1H), 7.5 (d, 1H), 7.7 (d, 1H), 7.76 (d, 1H), 7.88 (m, 1H).

EXAMPLE 38

Using an analogous procedure to that described in Example 5, 6-iodo-1-methyl-1,2,3,4-tetrahydroquinolin-2-one was reacted with 4-hydroxy-4-(2-mercaptothien-4-yl)-2,6-dimethyltetrahydropyran to give 4-hydroxy-2,6-dimethyl-4-[2-(1-methyl-2-oxo-1,2,3,4-tetrahydroquinolin-6-ylthio)thien-4-yl]tetrahydropyran in 28% yield;

NMR Spectrum: 1.1 (s, 3H), 1.43 (s, 3H), 1.5 (broad s, 1H), 1.7 (m, 3H), 2.09 (m, 1H), 2.55 (m, 2H), 2.79 (m, 2H), 3.25 (s, 3H), 4.15 (m, 2H), 6.8 (m, 1H), 7.05 (m, IH), 7.15 (m, 1H), 7.2 (m, 2H).

The 4-hydroxy-4-(2-mercaptothien-4-yl)-2,6-dimethyltetrahydropyran used as a starting material was obtained as follows:

The procedures described in the portion of Example 36 which are concerned with the preparation of starting materials were repeated except that 2,6-dimethyltetrahydropyran-4-one was used in place of 2,2-dimethyltetrahydropyran-4-one. There was thus obtained the required starting material which was used without further purification.

EXAMPLE 39

Using an analogous procedure to that described in Example 4, 4-hydroxy-2,6-dimethyl-4-[2-(1-methyl-2-oxo-1,2,3,4-tetrahydroquinolin-6-ylthio)thien-4-yl]tetrahydropyran was oxidised to give 4-hydroxy-2,6-dimethyl-4-[2-(1-methyl-2-oxo-1,2,3,4 -tetrahydroquinolin-6-ylsulphonyl)thien-4-yl]tetrahydropyran in 83% yield;

NMR Spectrum: 1.2 (s, 3H), 1.5 (s, 3H), 1.5–2.0 (m, 5H), 2.12 (m, 1H), 2.70 (m, 2H), 2.96 (m, 2H), 3.36 (s, 3H), 4.2 (m, 2H), 7.08 (m, 1H), 7.5 (d, 1H), 7.7 (d, 1H), 7.75 (m, 1H), 7.88 (m, 1H).

EXAMPLE 40

Using an analogous procedure to that described in Example 5, 6-iodo-1-methyl-1,2,3,4-tetrahydroquinolin-2-one was reacted with 3-hydroxy-3-(2-mercaptothien-4-yl)-8-oxabicyclo[3,2,1]octane to give 3-hydroxy-3-[2-(1-methyl-2-oxo-1,2,3,4-tetrahydroquinolin-6 -ylthio)thien-4-yl]-8-oxabicyclo[3,2,1] octane in 28% yield.

NMR Spectrum: 1.7–1.8 (m, 4H), 2.05 (m, 2H), 2.25 (m, 2H), 2.55 (m, 2H), 2.85 (m, 2H), 3.2 (s, 3H), 4.35 (m, 2H), 7.0–7.2 (m, 3H), 7.25 (d, 1H), 7.4 (d, 1H).

The 3-hydroxy-3-(2-mercaptothien-4-yl)-8-oxabicyclo[3,2,1]octane used as a starting material was obtained as follows:

A mixture of 8-oxabicyclo[3,2,1]oct-6-en-3-one (*J. Chem. Res.*(S), 1981, 246; 3.2 g), 10% palladium-on-carbon catalyst (0.45 g), water (2 ml) and ethanol (25 ml) was stirred under an atmosphere of hydrogen for 5 hours. The mixture was filtered and the filtrate was evaporated. The residue was partitioned between diethyl ether and brine. The organic phase was dried (MgSO$_4$) and evaporated. There was thus obtained 8-oxabicyclo[3,2,1]octan-3-one (2.84 g).

The procedures described in the portion of Example 36 which are concerned with the preparation of starting materials were repeated except that 8-oxabicyclo[3,2,1]octan-3-one was used in place of 2,2-dimethyltetrahydropyran-4-one. There was thus obtained 3-hydroxy-3-(2-mercaptothien-4-yl)-8-oxabicyclo[3,2,1]octane in 35% yield.

EXAMPLE 41

Using an analogous procedure to that described in Example 26 except that a catalytic amount (0.01 g) of potassium iodide was added to the reaction mixture, 6-mercapto-1-methyl-1,2,3,4-tetrahydroquinolin-2-one was reacted with 4-(2-chlorothiazol-5-yl)-4-hydroxy2,2-dimethyltetrahydropyran to give 4-hydroxy-2,2-dimethyl-4 -[2-(1-methyl-2-oxo-1,2,3,4-tetrahydroquinolin-6-ylthio)thiazol-5-yl]tetrahydropyran in 92% yield as a foam;

NMR Spectrum: 1.05 (s, 3H), 1.3 (s, 3H), 1.55–1.9 (m, 4H), 2.55 (m, 2H), 2.9 (m, 2H), 3.3 (s, 3H), 3.55 (m, 1H), 3.85 (m, 1H), 5.6 (broad s, 1H), 7.0–7.5 (m, 4H).

The 4-(2-chlorothiazol-5-yl)-4-hydroxy-2,2-dimethyltetrahydropyran used as a starting material was obtained as follows:

A solution of 2-chlorothiazole (0.75 g) in diethyl ether (8 ml) and n-butyl-lithium (1.4M in hexane, 4.5 ml) were added simultaneously but separately to diethyl ether (8 ml) which had been cooled to −80° C. The mixture was stirred at −75° C. for 10 minutes and then allowed to warm to −30° C. The mixture was recooled to −80° C. and a solution of 2,2-dimethyltetrahydropyran-4-one (0.76 g) in diethyl ether (5 ml) was added. The mixture was stirred and allowed to warm to −30° C. The mixture was poured onto a mixture of ice and a saturated aqueous ammonium chloride solution. The organic solution was washed with brine, dried (MgSO$_4$) and evaporated. The residue was purified by column chromatography using a 10:3 mixture of hexane and ethyl acetate as eluent. There was thus obtained 4-(2-chlorothiazol-5-yl)-4-hydroxy2,2-dimethyltetrahydropyran (0.67 g, 46%) as an oil;

NMR Spectrum: 1.2 (s, 3H), 1.45 (s, 3H), 1.8–2.15 (m, 4H), 3.75 (m, 1H), 4.1 (m, 1H), 7.38 (s, 1H).

EXAMPLE 42

Using an analogous procedure to that described in Example 26 except that a catalytic amount (0.01 g) of potassium iodide was added to the reaction mixture, 8-mercapto-[-methyl-1,2,3,4-tetrahydroquinolin-2-one was reacted with 4-(2-chlorothiazol-5-yl)-4-hydroxy2,6-dimethyltetrahydropyran to give 4-hydroxy-2,6-dimethyl-4-[2-(1-methyl-2-oxo-1,2,3,4 -tetrahydroquinolin-6-ylthio)thiazol-5-yl]tetrahydropyran in 53% yield as a foam;

NMR Spectrum: 1.2 (s, 3H), 1.5 (s, 3H), 1.7–1.9 (m, 3H), 2.15 (m, 1H), 2.66 (m, 2H), 2.95 (m, 2H), 3.39 (s, 3H), 4.18 (m, 2H), 7.0 (d, 1H), 7.5 (m, 2H), 7.55 (m, 1H).

The 4-(2-chlorothiazol-5-yl)-4-hydroxy-2,6-dimethyltetrahydropyran used as a starting material was obtained as follows:

The procedure described in the portion of Example 41 which is concerned with the preparation of starting materials was repeated except that 2,6-dimethyltetrahydropyran-4-one was used in place of 2,2-dimethyltetrahydropyran-4-one. There was thus obtained the required starting material in 77% yield.

NMR Spectrum: 1.2 (s, 3H), 1.5 (s, 3H), 1.7–2.0 (m, 3H), 2.16 (m, 2H), 4.2 (m, 2H), 7.38 (s, 1H).

EXAMPLE 43

Using an analogous procedure to that described in Example 5, 7-iodo-1-methyl-2,3,4,5-tetrahydro-1H-benzo[b]azepin-2-one was reacted with 3-hydroxy-3-(2-mercaptothien-4-yl)-8-oxabicyclo[3,2,1]octane to give 3-hydroxy-3-[2-(1-methyl-2-oxo-2,3,4,5-tetrahydro-1-benzo[b] -azepin-7-ylthio)thien-4-yl]-8-oxabicyclo[3,2,1]octane in 85% yield as an oil;

NMR Spectrum: 1.75–1.9 (m, 3H), 1.95 (m, 2H), 2.15 (m, 2H), 2.25–2.4 (m, 6H), 2.65 (t, 2H), 3.3 (s, 3H), 4.5 (m, 2H), 7.08 (m, 3H), 7.27 (m, 2H).

The 7-iodo-1-methyl-2,3,4,5-tetrahydro-1H-benzo[b]azepin-2-one used as a starting material was obtained as follows:

Sodium azide (3.9 g) was added portionwise during 1 hour to a stirred mixture of 1,2,3,4-tetrahydronaphthalen-1-one (8 g) and polyphosphoric acid (110 ml). The mixture was warmed slowly to 50° C. and stirred for 5 hours. The mixture was cooled to ambient temperature and poured onto a mixture of ice and water. The mixture was neutralised by the addition of a concentrated (40% weight/volume) aqueous sodium hydroxide solution and extracted with methylene chloride. The organic solution was washed with water, dried (MgSO$_4$) and evaporated. The residue was triturated under diethyl ether. There was thus obtained 2,3,4,5-tetrahydro-1H-benzolblazepin-2-one (5.4 g), m.p. 137°–39° C.

Sodium hydride (60% dispersion in mineral oil, 0.82 g) was added portionwise to a stirred solution of 2,3,4,5-tetrahydro-1H-benzo[b]azepin-2-one (3 g) in DMF (100 ml) which had been cooled to 0° C. The mixture was stirred at 10° C. for 1 hour. A solution of methyl iodide (2.64 g) in THF (8 ml) was added dropwise and the mixture was stirred at ambient temperature for 2 hours. The mixture was evaporated and the residue was partitioned between ethyl acetate and water. The organic solution was washed with water, dried (Na$_2$SO$_4$) and evaporated. The residue was purified by column chromatography using a 1:1 mixture of toluene and ethyl acetate as eluent. There was thus obtained 1-methyl-2,3,4,5-tetrahydro-1H-benzo[b]azepin-2-one (2.25 g, 69%) as a liquid.

A mixture of a portion (2 g) of the material so obtained, iodine (1.27 g), iodic acid (1.86 g), concentrated sulphuric acid (1.5 ml) and acetic acid (8.5 ml) was stirred and heated to 95° C. for 2 hours. The mixture was cooled to ambient temperature and partitioned between ethyl acetate and a saturated aqueous sodium bicarbonate solution. The organic solution was washed with an aqueous sodium thiosulphate solution, dried (Na$_2$SO$_4$) and evaporated. The residue was purified by column chromatography using a 3:2 mixture of hexane and ethyl acetate as eluent. There was thus obtained 7-iodo-1-methyl2,3,4,5 -tetrahydro-1H-benzo[b]azepin-2-one (2.1 g), m.p. 124–126° C.

EXAMPLE 44

Using an analogous procedure to that described in Example 4, 3-hydroxy-3-[2-(1-methyl-2-oxo-2,3,4,5-tetrahydro-1H-benzo[b]azepin-7 -ylthio)thien-4-yl-8-oxabicyclo[3,2,1]octane was oxidised to give 3-hydroxy-3-[2-(1-methyl-2-oxo-2,3,4,5-tetrahydro-1H-benzo[b] -azepin-7-ylsulphonyl)thien-4-yl-8-oxabicyclo[3,2,13octane in 73% yield;

NMR Spectrum: (CDCl$_3$ +CD$_3$CO$_2$D) 1.8–2.0 (m, 4H), 2.2–2.4 (m, 8H), 2.75–2.86 (t, 2H), 3.4 (s, 3H), 4.5–4.6 (m, 2H), 7.35 (d, 1H), 7.55 (d, 1H), 7.7 (d, 1H), 7.85 (d, 1H), 7.95 (m, 1H).

EXAMPLE 45

Using an analogous procedure to that described in Example 6, 6-mercapto-1-methyl-1,2,3,4-tetrahydroquinolin-2-one was reacted with (2SR,4RS)-2-ethyl-4-hydroxy-4-(3-iodophenyl)tetrahydropyran to give (2SR,4RS)-2-ethyl-4-hydroxy-4-[3-(1-methyl-2-oxo-1,2,3,4 -tetrahydroquinolin-6-ylthio)phenyl]tetrahydropyran in 63% yield as a gum;

NMR Spectrum: 0.95 (t, 3H), 1.4–1.8 (m, 6H), 2.1 (m, 1H). 2.65 (m, 2H), 2.85 (m, 2H), 3.35 (s, 3H), 3.7 (m, 1H), 3.95 (m, 2H), 6.85 (d, 1H), 7.12 (m, 1H), 7.2–7.4 (m, 4H), 7.5 (m, 1H).

The (2SR,4RS)-2-ethyl-4-hydroxy-4-(3-iodophenyl)tetrahydropyran used as a starting material was obtained by repetition of the portion of Example 6 which is concerned with the preparation of starting materials except that 2-ethyltetrahydropyran-4-one (Chem. Ber., 1955, 88, 1053) was used in place of (2S)-2-methyltetrahydropyran-4-one. There was thus obtained the required starting material in 63% yield as an oil.

EXAMPLE 46 using an analogous procedure to that described in Example 5, 6-iodo-1-methyl-2-oxo-1,2,3,4-tetrahydroquinazoline was reacted with (2S,4R)-4-(tert-butyldimethylsilyloxy)-4-(3-mercaptophenyl)-2methyltetrahydropyran to give (2S,4R)-4-(tert-butyldimethylsilyloxy)2-methyl-4-[3-(1-methyl-2-oxo-1,2,3,4-tetrahydroquinazolin-6-ylthio)phenyl]tetrahydropyran in 41% yield as a foam. A mixture of the material so formed (0.12 g) and tetrabutylammonium fluoride (1M in THF, 5 ml) was stirred and heated to reflux for 2 hours. The mixture was cooled to ambient temperature and partitioned between ethyl acetate and water. The organic solution was dried (Na$_2$SO$_4$) and evaporated. The residue was purified by column chromatography using increasingly polar mixtures of methylene chloride and methanol as eluent. There was thus obtained (2S,4R)-4-hydroxy-2-methyl-4-[3-(1-methyl-2-oxo-1,2,3,4 -tetrahydroquinazolin-6-ylthio)phenyl]tetrahydropyran (0.07 g) as a gum;

NMR Spectrum: 1.2 (d, 3H), 1.5–1.8 (m, 4H), 2.05 (m, 1H), 3.3 (s, 3H), 3.8–4.05 (m, 3H), 4.38 (s, 2H), 5.0 (broad s, 1H), 6.82 (d, 1H), 7.05 (m, 1H), 7.12 (m, 1H), 7.2–7.37 (m, 3H), 7.42 (m, 1H).

The 6-iodo-1-methyl-2-oxo-1,2,3,4-tetrahydroquinazoline used as a starting material was obtained as follows: A mixture of 5-iodoanthranilic acid (10.5 g), N-hydroxysuccinimide (4.92 g), N,N'-dicyclohexylcarbodiimide (9 g) and ethyl acetate (200 ml) was stirred at ambient temperature for 2 hours. The mixture was filtered and the filtrate was evaporated. A saturated solution of ammonia in methanol (200 ml) was added and the mixture was stirred at ambient temperature for 18 hours. The mixture was evaporated and the residue was partitioned between ethyl acetate and 1N aqueous sodium hydroxide solution. The organic solution was washed with brine, dried (MgSO$_4$) and evaporated. There was thus obtained 5-iodoanthranilamide (6.7 g) which was used without further purification.

A mixture of a portion (1.4 g) of the material so obtained and a borane: THF complex (1M in THF, 16 ml) was stirred at ambient temperature for 18 hours. The mixture was evaporated. Methanol (20 ml) was added to the residue and the mixture was re-evaporated. A 2N aqueous hydrochloric acid solution (30 ml) was added to the residue and the mixture was stirred at ambient temperature for 30 minutes. The mixture was basified to pH9 by the addition of 2N aqueous sodium hydroxide solution and extracted with methylene chloride. The organic solution was washed with brine, dried (Na$_2$SO$_4$) and evaporated. The residue was triturated under diethyl ether. There was thus obtained 2-amino-5-iodobenzylamine (0.95 g, 73%).

After repetition of the above mentioned reactions, a mixture of 2-amino-5-iodobenzylamine (2.1 g), 1,1'-carbonyldiimidazole (1.64 g) and THF (20 ml) was stirred and heated to reflux for 30 hours. The mixture was cooled to ambient temperature and the precipitate was isolated. There was thus obtained 6-iodo-2-oxo-1,2,3,4-tetrahydroquinazoline (1.88 g, 91%), m.p. 242–244° C.

A mixture of a portion (0.5 g) of the material so obtained, sodium hydride (60% dispersion in mineral oil, 0.07 g) and DMF (5 ml) was stirred at ambient temperature for 30 minutes. Methyl iodide (0.24 ml) was added and the mixture was stirred at ambient temperature for 2 hours. The mixture was partitioned between ethyl acetate and a saturated aqueous ammonium chloride solution. The organic solution was washed with brine, dried (Na$_2$SO$_4$) and evaporated. There was thus obtained 6-iodo-1-methyl-2-oxo-1,2,3,4-tetrahydroquinazoline (0.3 g, 57%), m.p. 175°–178° C.

The (2S,4R)-4-(tert-butyldimethylsilyloxy)-4-(3-mercaptophenyl)-2-methyltetrahydropyran used as a starting material was obtained as follows:

Using an analogous procedure to that described in the portion of Example 6 which is concerned with the preparation of starting materials, 1,3-dibromobenzene was reacted with (2S)-2-methyltetrahydropyran-4-one to give (2S,4R)-4-hydroxy-4-(3-bromophenyl)-2-methyltetrahydropyran in 66% yield as an oil.

Using an analogous procedure to that described in the portion of Example 18 which is concerned with the preparation of starting materials, the 4-(3-bromophenyl)-2-methyltetrahydropyran so obtained was reacted with tert-butyldimethylsilyl chloride to give (2S,4R)-4 -(tert-butyldimethylsilyloxy)-4-(3-bromophenyl)-2-methyltetrahydropyran in 78% yield as an oil.

A solution of the material so obtained (0.96 g) in THF (5 ml) was cooled to −80° C. and n-butyl-lithium (1.6M in hexane, 1.6 ml) was added dropwise. The mixture was stirred at −80° C. for 30 minutes. Sulphur (0.08 g) was added and the mixture was stirred at −80° C. for 30 minutes. A 2N aqueous sodium hydroxide solution (20 ml) was added and the mixture was allowed to warm to ambient temperature. The mixture was washed with diethyl ether, acidified to pH3 by the addition of 2N aqueous hydrochloric acid solution and extracted with ethyl acetate. The organic solution was washed with brine, dried (Na$_2$SO$_4$) and evaporated. There was thus obtained (2S,4R)-4-(tert-butyldimethyl- silyloxy)-4-(3-mercaptophenyl)-2-methyltetrahydropyran (0.22 g, 26%) as an oil which was used without further purification.

EXAMPLE 47

Using an analogous procedure to that described in Example 5, 6-iodo-1,3-dimethyl-2-oxo-1,2,3,4-tetrahydroquinazoline was reacted with (2S,4R)-4-hydroxy-4-(2-mercaptothien-4-yl)-2-methyltetrahydropyran to give (2S,4R)-4-hydroxy-2-methyl-4-[2-(1,3-dimethyl-2-oxo-1,2,3,4 -tetrahydroquinazolin-6-ylthio)thien-4-yl]tetrahydropyran in 74% yield as a gum;

NMR Spectrum: 1.2 (d, 3H), 1.5–1.85 (m, 4H), 2.05 (m, 1H), 3.02 (s, 3H), 3.3 (s, 3H), 3.8–4.05 (m, 3H), 4.32 (s, 2H), 6.75 (d, 1H), 7.05 (d, 1H), 7.2–7.3 (m, 3H).

The 6-iodo-1,3-dimethyl-2-oxo-1,2,3,4-tetrahydroquinazoline used as a starting material was obtained as follows:

Sodium hydride (60% dispersion in mineral oil, 0.24 g) was added portionwise to a stirred mixture of 6-iodo-2-oxo-1,2,3,4-tetrahydroquinazoline (0.55 g), methyl iodide (0.71 ml) and DMF (5 ml) and the resultant mixture was stirred at ambient temperature for 30 minutes. The mixture was partitioned between ethyl acetate and a saturated aqueous ammonium chloride solution. The organic solution was washed with brine, dried (Na$_2$SO$_4$) and evaporated. The residue was triturated under diethyl ether. There was thus obtained 6-iodo-1,3-dimethyl-2-oxo-1,2,3,4-tetrahydroquinazoline (0.38 g, 63%) which was used without further purification.

EXAMPLE 48

Potassium tert-butoxide (0.212 g) was added to a stirred solution of (2S,4R)-4-hydroxy-4-(2-mercaptothien-4-yl)-2-methyltetrahydropyran (0.4 g) in DMSO (5 ml) and the mixture was stirred at ambient temperature for 5 minutes. 6-Iodo-1-methyl-2-thioxo-1,2,3,4tetrahydroquinoline (0.526 g) and tetrakis(triphenylphosphine)palladium(O) (0.21 g) were added in turn and the mixture was stirred and heated to 90° C. for 2.5 hours. A further portion of the palladium catalyst (0.1 g) was added and the mixture was heated to 90° C. for a further hour. The mixture was cooled to ambient temperature and partitioned between ethyl acetate and water. The organic phase was washed with brine, dried (MgSO$_4$) and evaporated. The residue was purified by column chromatography using a 1:1 mixture of methylene chloride and diethyl ether as eluent. There was thus obtained (2S,4R)-4-hydroxy-2-methyl-4-[2-(1-methyl-2-thioxo-1,2,3,4-tetrahydroquinolin-6-ylthio)thien-4-yl]tetrahydropyran as a solid (0.09 g, 13%);

NMR Spectrum: 1.2 (d, 3H), 1.7 (m, 3H), 2.05 (m, 1H), 2.72 (m, 2H), 3.16 (m, 2H), 3.87 (s, 3H), 3.92 (m, 3H), 7.02 (m, 2H), 7.13 (m, 1H), 7.30 (m, 2H).

The 6-iodo-1-methyl-2-thioxo-1,2,3,4-tetrahydroquinoline used as a starting material was obtained as follows:

A mixture of 6-iodo-1-methyl-1,2,3,4-tetrahydroquinolin-2-one (0.6 g), 2,4-bis(4-methoxyphenyl)-1,3-dithia-2,4-diphosphetane-2,4disulphide (Lawesson's Reagent, 0.49 g) and toluene (7 ml) was stirred and heated to 100° C. for 1 hour. The mixture was cooled to ambient temperature and evaporated. The residue was purified by column chromatography using a 4:1 mixture of petroleum ether (b.p. 40–60° C.) and methylene chloride as eluent. There was thus obtained 6-iodo-1-methyl-2-thioxo- 1,2,3,4-tetrahydroquinoline (0.42 g), m.p. 202°–204° C.;

NMR Spectrum: 2.76 (m, 2H), 3.17 (m, 2H), 3.86 (s, 3H), 6.88 (d, 1H), 7.50 (d, 1H), 7.61 (m, 1H).

EXAMPLE 49

Using an analogous procedure to that described in Example 3, 6-mercapto-1-methyl-2-thioxo-1,2,3,4-tetrahydroquinoline was reacted with (2S,4R)-4-(2-chlorothiazol-5-yl)-4-hydroxy-2-methyltetrahydropyran to give (2S,4R)-4-hydroxy-2-methyl-4-[2-(1-methyl-2-thioxo-1,2,3,4-tetrahydroquinolin-6-ylthio)thiazol-5-yl]tetrahydropyran as a foam (0.365 g, 45%);

NMR Spectrum: 1.19 (d, 3H), 1.6–2.1 (m, 5H), 2.83 (m, 2H), 3.22 (m, 2H), 3.86 (m, 3H), 3.90 (s, 3H), 7.17 (d, 1H), 7.44 (d, 1H), 7.52 (d, 1H), 7.55 (m, 1H).

The 6-mercapto-1-methyl-2-thioxo-1,2,3,4-tetrahydroquinoline used as a starting material was obtained as follows:

A mixture of di-(1-methyl-2-oxo-1,2,3,4-tetrahydroquinolin-6-yl) disulphide (1 g), 2,4-bis(4-methoxyphenyl)-1,3-dithia-2,4 -diphosphetane-2,4-disulphide (0.65 g) and toluene (10 ml) was stirred and heated to reflux for 1 hour. The mixture was evaporated and the residue was purified by column chromatography using methylene chloride as eluent. There was thus obtained di-(1-methyl-2-thioxo-1,2,3,4-tetrahydroquinolin-6-yl) disulphide (0.86 g, 79%), m.p. 180°–182° C.

The material so obtained was reacted with triphenylphosphine in the presence of concentrated hydrochloric acid using an analogous procedure to that described in the portion of Example 1 which is concerned with the preparation of starting materials. There was thus obtained 6-mercapto-1-methyl-2-thioxo-1,2,3,4-tetrahydroquinoline in 85% yield as a solid which was used without further purification.

EXAMPLE 50

Using an analogous procedure to that described in Example 5, 6-iodo-1-methyl-1,2,3,4-tetrahydroquinolin-2-one was reacted with (2RS,3SR)-3-hydroxy-3-(2-mercaptothien-4-yl)-2-methyltetrahydrofuran to give (2RS,3SR)-3-hydroxy-2-methyl-3-[2-(1-methyl-2-oxo-1,2,3,4 -tetrahydroquinolin-6-ylthio)thien-4-yl]tetrahydrofuran in 42% yield as a foam;

NMR Spectrum: 1.17 (d, 3H), 2.0 (broad s, 1H), 2.2–2.55 (m, 2H), 2.64 (m, 2H), 2.86 (m, 2H), 3.32 (s, 3H), 3.85–4.2 (m, 3H), 6.9 (d, 1H), 7.11 (d, 1H), 7.19 (m, 1H), 7.22 (d, 1H), 7.37 (d, 1H).

The (2RS,3SR)-3-hydroxy-3-(2-mercaptothien-4-yl)-2-methyltetrahydrofuran used as a starting material was obtained as follows:

A mixture of (2RS,3SR)-3-hydroxy-2-methyl-3-(2 -methylthiothien-4-yl)tetrahydrofuran (European Patent Application No. 0 555 068, Example 80 thereof; 0.44 g), sodium methanethiolate (0.21 g) and DMF (6.3 ml) was stirred and heated to 130° C. for 90 minutes. The mixture was cooled to ambient temperature and partitioned between ethyl acetate and water. The mixture was acidified by the addition of 1M aqueous citric acid solution. The organic solution was washed with water and with brine, dried (MgSO$_4$) and evaporated. There was thus obtained (2RS,3SR)-3-hydroxy-3-(2-mercaptothien-4-yl)-2-methyltetrahydrofuran (0.36 g, 86%) which was used without further purification.

EXAMPLE 51

The following illustrate representative pharmaceutical dosage forms containing the compound of formula I, or a pharmaceutically-acceptable salt thereof (hereafter compound X), for therapeutic or prophylactic use in humans:

| | | mg/tablet |
|---|---|---|
| (a) | Tablet I | |
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |

-continued

| | |
|---|---|
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

We claim:

1. An ether derivative of the formula I $$Q^1\text{---}X\text{---}Ar\text{---}Q^2 \quad \text{I}$$

wherein $Q^1$ is a 9-, 10- or 11-membered bicyclic heterocyclic moiety having one or two nitrogen heteroatoms and optionally having one further heteroatom selected from nitrogen, oxygen and sulphur, and $Q^1$ may optionally bear up to four substituents selected from halogeno, hydroxy, cyano, formyl, oxo, thioxo, (1–4C)alkyl, (3–4C)alkenyl, (3–4C)alkynyl, (1–4C)alkoxy, fluoro-(1–4C)alkyl, hydroxy-(1–4C)alkyl, (2–5C)alkanoyl, phenyl, benzoyl and benzyl, and wherein said phenyl, benzoyl and benzyl substituents may optionally bear one or two substituents selected from halogeno, (1–4C)alkyl and (1–4C)alkoxy;

X is oxy, thio, sulphinyl or sulphonyl;

Ar is phenylene, pyridinediyl, pyrimidinediyl, thiophenediyl, furandiyl, thiazolediyl, oxazolediyl, thiadiazolediyl or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino; and $Q^2$ is selected from the group consisting of the formulae II and III:

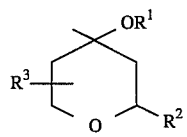   II

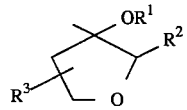   III wherein $R^1$ is hydrogen, (2–5C)alkanoyl or benzoyl, and wherein said benzoyl group may optionally bear one or two substituents selected from halogeno, (1–4C)alkyl and (1–4C)alkoxy;

$R^2$ is (1–4C)alkyl; and $R^3$ is hydrogen or (1–4C)alkyl;

or $R^2$ and $R^3$ are linked to form a methylene, vinylene, ethylene or trimethylene group;

or a pharmaceutically-acceptable salt thereof.

2. An ether derivative of the formula I as claimed in claim 1 wherein $Q^1$ is 2-oxoindolinyl, 2-oxo-1,2-dihydroquinolinyl, 2-oxo-1,2,3,4-tetrahydroquinolinyl or 2-oxo-2,3,4,5-tetrahydro-1H-benzo[b]azepinyl which may optionally bear one, two or three substituents selected from fluoro, chloro, methyl, ethyl, allyl and 2-propynyl;

X is thio, sulphinyl or sulphonyl;

Ar is 1,3-phenylene which may optionally bear one or two fluoro substituents or Ar is 2,4- or 2,5-thiophenediyl or 2,4- or 2,5-thiazolediyl; and $Q^2$ is a group of the formula II wherein
$R^1$ is hydrogen;
$R^2$ is methyl or ethyl; and
$R^3$ is hydrogen or methyl;
or $R^2$ and $R^3$ are linked to form an ethylene group;

or a pharmaceutically-acceptable salt thereof.

3. An ether derivative of the formula I as claimed in claim 1 wherein $Q^1$ is 2-oxoindolinyl which may optionally bear one, two or three substituents selected from fluoro, chloro, methyl, ethyl, allyl and 2-propynyl;

X is thio, sulphinyl or sulphonyl;

Ar is 1,3-phenylene which may optionally bear one or two fluoro substituents or Ar is 2,4- or 2,5-thiophenediyl or 2,4- or 2,5-thiazolediyl; and $Q^2$ is a group of the formula II wherein
$R^1$ is hydrogen;
$R^2$ is methyl or ethyl; and
$R^3$ is hydrogen or methyl;

or a pharmaceutically-acceptable salt thereof.

4. An ether derivative of the formula I as claimed in claim 1 wherein

Q is 2-oxoindolin-5-yl, 2-oxo-1,2-dihydroquinolin-6-yl, 2-oxo-1,2,3,4-tetrahydroquinolin-6-yl or 2-oxo-2,3,4,5-tetrahydro-1 H-benzo[b]azepin-7-yl which optionally bears at the 1-position a substituent selected from methyl, ethyl, allyl and 2-propynyl and which also optionally bears a further substituent selected from fluoro, chloro and methyl;

X is thio, sulphinyl or sulphonyl;

Ar is 1,3-phenylene or 5-fluoro-1,3-phenylene or Ar is 2,4-thiophenediyl (with the X group in the 2-position), 2,5-thiophenediyl, 2,4-thiazolediyl (with the X group in the 2-position) or 2,5-thiazolediyl (with the X group in the 2-position); and $Q^2$ is a group of the formula IV

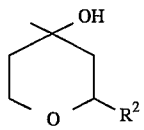

IV wherein $R^2$ is methyl;

or a pharmaceutically-acceptable salt thereof.

5. An ether derivative of the formula I as claimed in claim 4 wherein $Q^1$ is 1-methyl-2-oxoindolin-5-yl, 1-methyl-2-oxo-1,2-dihydroquinolin-6-yl, 1-allyl-2-oxo-1,2,3,4-tetrahydroquinolin-6-yl, 1-ethyl-2-oxo-1,2,3,4-tetrahydroquinolin-6-yl, 1-methyl-2-oxo-1,2,3,4-tetrahydroquinolin-6-yl, 1-(2-propynyl)-2-oxo-1,2,3,4-tetrahydroquinolin-6-yl, 8-chloro-1-methyl-2-oxo-1,2,3,4-tetrahydroquinolin-6-yl, 7-fluoro-1-methyl-2-oxo-1,2,3,4-tetrahydroquinolin-6-yl, 8-fluoro-1methyl-2-oxo-1,2,3,4-tetrahydroquinolin-6-yl, 1,8-dimethyl-2-oxo-1,2,3,4-tetrahydroquinolin-6-yl or 1-methyl-2-oxo-2,3,4,5-tetrahydro-1H-benzo[b]azepin-7-yl;

X is thio, sulphinyl or sulphonyl;

Ar is 2,4-thiophenediyl (with the X group in the 2-position), 2,5-thiophenediyl or 2,5-thiazolediyl (with the X group in the 2-position); and $Q^2$ is a group of the formula IV wherein $R^2$ is methyl;

or a pharmaceutically-acceptable salt thereof.

6. An ether derivative of the formula I as claimed in claim 4 wherein $Q^1$ is 1-methyl-2-oxoindolin-5-yl, 1-methyl-2-oxo-1,2-dihydroquinolin-6-yl, 1-allyl-2-oxo-1,2,3,4-tetrahydroquinolin-6-yl, 1-ethyl-2-oxo-1,2,3,4-tetrahydroquinolin-6-yl, 1-methyl-2-oxo-1,2,3,4-tetrahydroquinolin-6-yl, 1-(2-propynyl)-2-oxo-1,2,3,4-tetrahydroquinolin-6-yl, 8-chloro-1-methyl-2-oxo-1,2,3,4-tetrahydroquinolin-6-yl, 7-fluoro-1-methyl-2-oxo-1,2,3,4-tetrahydroquinolin-6-yl, 8-fluoro-1-methyl-2-oxo-1,2,3,4-tetrahydroquinolin-6-yl, 1,8-dimethyl-2-oxo-1,2,3,4-tetrahydroquinolin-6-yl or 1-methyl-2-oxo-2,3,4,5-tetrahydro-1H-benzo[b]azepin-7-yl;

X is thio, sulphinyl or sulphonyl;

Ar is 1,3-phenylene or 5-fluoro-1,3-phenylene; and $Q^2$ is a group of the formula IV wherein $R^2$ is methyl;

or a pharmaceutically-acceptable salt thereof.

7. The ether derivative of the formula I, or a pharmaceutically-acceptable salt thereof, as claimed in claim 1 selected from:

(2S,4R)-4-[5-fluoro-3-(1-methyl-2-oxo-1,2,3,4-tetrahydroquinolin-6-ylthio)phenyl]-4-hydroxy-2-methyltetrahydropyran and (2S,4R)-4-[5-fluoro-3-(1-methyl-2-oxo-1,2,3,4-tetrahydroquinolin-6 -ylsulphonyl)phenyl]-4-hydroxy-2-methyltetrahydropyran.

8. The ether derivative of the formula I, or a pharmaceutically-acceptable salt thereof as claimed in claim 1 selected from:

(2S,4R)-4-hydroxy-2-methyl-4-[2-(1-methyl-2-oxo-1,2,3,4-tetrahydroquinolin-6-ylthio)thiazol-5-yl]tetrahydropyran, (2S,4R)-4-hydroxy-2-methyl-4-[2-(1-methyl-2-oxo-1,2,3,4-tetrahydroquinolin-6-ylsulphonyl)thiazol-5-yl]tetrahydropyran, (2S,4R)-4-[2-(7-fluoro-1-methyl-2-oxo-1,2,3,4-tetrahydroquinolin- 6-ylthio)thiazol-5-yl]-4-hydroxy-2-methyltetrahydropyran, (2S,4R)-4-hydroxy-2-methyl-4-[2-(1-methyl-2-oxoindolin-5-ylthio)thiazol-5-yl]tetrahydropyran, (2S,4R)-4-hydroxy-2-methyl-4-[2-(1-methyl-2-oxo-1,2,3,4-tetrahydroquinolin-6-ylthio)thien-4-yl]tetrahydropyran, (2S,4R)-4-hydroxy-2-methyl-]2-(1-methyl-2-oxo-1,2,3,4-tetrahydroquinolin-6 -ylsulphonyl)thien-4-yl]tetrahydropyran, (2S,4R)-4-hydroxy-2-methyl-4-[2-(1-methyl-2-oxo-1,2,3,4-tetrahydroquinolin-6-ylthio)thien-5-yl]tetrahydropyran, (2S,4R)-4-hydroxy-2-methyl-4-[2-(1-methyl-2-oxo-1,2-dihydroquinolin-6-ylthio)thien-4-yl]tetrahydropyran, (2S,4R)-4-hydroxy-2-methyl-4-[2-(1,8-dimethyl-2-oxo-1,2,3,4 -tetrahydroquinolin-6-ylthio)thien-4-yl]tetrahydropyran, 4-[2-(8-fluoro-1methyl-2-oxo-1,2,3,4-tetrahydroquinolin- 6-ylthio)thien-4-yl]-4-hydroxy-2-methyltetrahydropyran, 4-[2-(7-fluoro-1methyl-2-oxo-1,2,3,4-tetrahydroquinolin- 6-ylthio)thien-4-yl]-4-hydroxy-2-methyltetrahydropyran, (2S,4R)-4-hydroxy-2-methyl-4-[2-(1-methyl-2-oxoindolin-5 -ylthio)thien-4-yl]tetrahydropyran, (2S,4R)-4-hydroxy-2-methyl-4-[3-(1-methyl-2-oxo-1,2,3,4 -tetrahydroquinolin-6-ylthio)phenyl]tetrahydropyran, (2S,4R)-4-hydroxy-2-methyl-4-[3-(1-methyl-2-oxo-1,2,3,4 -tetrahydroquinolin-6-ylsulphonyl)phenyl]tetrahydropyran, (2S,4R)-4-[3-(1-ethyl-2-oxo-1,2,3,4-tetrahydroquinolin-6 -ylthio)phenyl]-4-hydroxy-2-methyltetrahydropyran, (2S,4R )-4-[3-(7-fluoro-1-methyl-2-oxo-1,2,3,4-tetrahydroquinolin-6 -ylthio)phenyl]-4-hydroxy-2-methyltetrahydropyran, (2S,4R)-4-hydroxy-2-methyl-4-[3-(1-methyl-2-oxo-1,2-dihydroquinolin-6 -ylthio)phenyl]tetrahydropyran, (2S,4R)-4-[3-(8-chloro-1-methyl-2-oxo-1,2,3,4-tetrahydroquinolin-6 -ylthio)phenyl]-4-hydroxy-2-methyltetrahydropyran and (2S,4R )-4-hydroxy-2-methyl-4-[3-(1-methyl-2-oxoindolin-5 -ylthio)phenyl]tetrahydropyran.

9. The ether derivative of the formula I as claimed in claim 1 being:

(2S,4R)-4-hydroxy-2-methyl-4-[2-(1-methyl-2-oxoindolin-5 -ylthio)thien-4-yl]tetrahydropyran, or a pharmaceutically-acceptable salt thereof.

10. A pharmaceutical composition which comprises an ether derivative of the formula I, or a pharmaceutically-acceptable salt thereof, as claimed in any one of claims 1 to 9 in association with a pharmaceutically-acceptable diluent or carrier.

11. A method of treating a disease or medical condition mediated alone or in part by one or more leukotrienes which comprises administering to a warm-blooded animal requiring such treatment an effective amount of an ether derivative of the formula I, or a pharmaceutically-acceptable salt thereof, as claimed in any one of claims 1 to 6.

* * * * *